(12) United States Patent
Jessop

(10) Patent No.: US 8,283,385 B2
(45) Date of Patent: Oct. 9, 2012

(54) REVERSIBLY SWITCHABLE SURFACTANTS AND METHODS OF USE THEREOF

(75) Inventor: Philip G. Jessop, Kingston (CA)

(73) Assignee: Queen's University at Kingston, Kingston, ON (CA)

( * ) Notice: Subject to any disclaimer, the term of this patent is extended or adjusted under 35 U.S.C. 154(b) by 1273 days.

(21) Appl. No.: 11/599,623

(22) Filed: Nov. 15, 2006

(65) Prior Publication Data
US 2008/0197084 A1 Aug. 21, 2008

Related U.S. Application Data

(60) Provisional application No. 60/736,507, filed on Nov. 15, 2005, provisional application No. 60/736,840, filed on Nov. 16, 2005.

(30) Foreign Application Priority Data

Nov. 15, 2005 (CA) ..................................... 2527144

(51) Int. Cl.
| B01F 17/16 | (2006.01) |
| B01F 17/04 | (2006.01) |
| B01F 17/22 | (2006.01) |
| B01F 3/08 | (2006.01) |
| C07B 63/02 | (2006.01) |
| B01D 17/04 | (2006.01) |
| B01D 17/05 | (2006.01) |
| C07C 257/10 | (2006.01) |
| C07C 279/02 | (2006.01) |
| C07D 233/06 | (2006.01) |
| C07D 239/06 | (2006.01) |
| C07F 7/10 | (2006.01) |
| C08F 2/22 | (2006.01) |
| C08F 2/32 | (2006.01) |

(52) U.S. Cl. .............. 516/22; 516/23; 516/27; 516/55; 516/67; 516/71; 516/203; 516/924; 510/276; 510/350; 510/351; 510/423; 510/433; 510/499; 524/801

(58) Field of Classification Search .................. 564/225, 564/230; 516/203, 22, 23, 27, 55, 67, 71, 516/924; 510/276, 350, 351, 423, 433, 499; 556/410; 524/801; 544/242; 548/347.1
See application file for complete search history.

(56) References Cited

U.S. PATENT DOCUMENTS
2,630,386 A * 3/1953 Walker ........................... 426/69
(Continued)

FOREIGN PATENT DOCUMENTS
JP 2004-59750 2/2004

OTHER PUBLICATIONS
Heldebrant et al, "The Reaction of 1,8-Diazabicyclo[5.4.0]undec-7-ene (DBU) with Carbon Dioxide", Journal of Organic Chemistry, 2005, 70, pp. 5335-5338 (Published on web May 26, 2005).*

(Continued)

Primary Examiner — Daniel S Metzmaier
(74) Attorney, Agent, or Firm — Angela Lyon; Carol Miernicki Steeg

(57) ABSTRACT

Reversible switchable surfactants are provided. A surfactant is the salt of an amidine or guanidine:

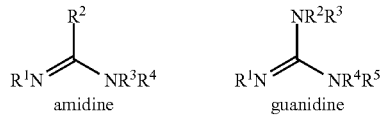

having at least one R group that is a hydrophobic moiety selected from the group consisting of higher aliphatic moiety, higher siloxyl moiety, higher aliphatic/siloxyl moiety, aliphatic/aryl moiety, siloxyl/aryl moiety, and aliphatic/siloxyl/aryl moiety. The other R groups are smaller moieties such as H, $C_1$ to $C_4$ aliphatic or the like. The surfactant is turned on by a gas that liberates hydrogen ions, such as, for example, carbon dioxide, which liberates hydrogen ions in the presence of water. The surfactant is turned off by exposure to a flushing gas and/or heating. When "on" the surfactants are useful to stabilize emulsions, and when "off" they are useful to separate immiscible liquids or a liquid and a solid. The surfactants find uses in polymerization and in the oil industry.

18 Claims, 11 Drawing Sheets

U.S. PATENT DOCUMENTS

| | | | | |
|---|---|---|---|---|
| 3,060,007 | A | | 10/1962 | Freedman |
| 3,143,461 | A | * | 8/1964 | Berg .......................... 514/597 |
| 3,228,956 | A | | 1/1966 | Monroe |
| 3,598,800 | A | * | 8/1971 | Gatzi .......................... 546/229 |
| 4,499,274 | A | * | 2/1985 | Feth et al. ..................... 546/229 |
| 4,770,670 | A | * | 9/1988 | Hazbun et al. .................. 44/301 |
| 5,457,083 | A | * | 10/1995 | Muia et al. .................... 504/128 |
| 5,905,061 | A | * | 5/1999 | Patel .......................... 507/129 |
| 6,218,342 | B1 | * | 4/2001 | Patel .......................... 507/129 |
| 6,499,546 | B1 | * | 12/2002 | Freeman et al. ................ 175/66 |
| 6,890,969 | B2 | * | 5/2005 | Rabasco et al. ............... 523/122 |
| 7,700,533 | B2 | * | 4/2010 | Egbe et al. ................... 510/176 |
| 7,982,069 | B2 | * | 7/2011 | Jessop et al. ................. 564/230 |
| 2002/0099113 | A1 | * | 7/2002 | Rabasco et al. ............... 523/122 |
| 2006/0293208 | A1 | * | 12/2006 | Egbe et al. ................... 510/407 |
| 2007/0092801 | A1 | | 4/2007 | Tipton |
| 2008/0058549 | A1 | | 3/2008 | Jessop |
| 2009/0136402 | A1 | | 5/2009 | Heldebrant |
| 2010/0240566 | A1 | * | 9/2010 | Meine et al. .................. 510/499 |
| 2011/0076214 | A1 | * | 3/2011 | Yu et al. ..................... 564/225 |
| 2011/0257334 | A1 | * | 10/2011 | Jessop et al. ................. 564/225 |
| 2012/0116076 | A1 | * | 5/2012 | Jessop et al. ................. 540/579 |

OTHER PUBLICATIONS

Jessop et al, "Green Chemistry Reversible nonpolar-to-polar solvent", Nature, Aug. 25, 2005, 436, 7054, Research Library, p. 1102.*

Jaroszewska-Manaj, J. et al. "Amidines. Part 41. Effects of substitution . . . " J. Chem. Soc., Perkin Trans. 2, 1186-1191 (2001), (May 2001).

Oszczapowicz, J. et al., "Amidines. Part 13. Influence of Substitution" J. Chem. Soc., Perkin Trans. II, 1643-1646 (1984).

Scoggins, M.W., "A Rapid Gas Chromatographic Analysis of Diastereomeric Diamines." J. Chromatogr. Sci., 13:146-148 (Mar. 1975).

Defrise-Quertain, F., et al., "Vesicle formation by double long-chain amidines." J. Chem. Soc., Chem. Comm., 1060-1062 (1986).

Edwards, A., et al., "Mechanistic studies of the corrosion inhibitor oleic imidazoline." Corrosion Science 36(2): 315-325 (1994).

International Search Report for PCT/CA2006/001877 filed Nov. 15, 2006, (mailed Feb. 16, 2007).

López, D.A., et al., "Inhibitors performance in $CO_2$ corrosion EIS studies on the interaction between their molecular structure and steel microstructure." Corrosion Science 47: 735-755 (2005).

Pincet, F., et al., "Spontaneous and reversible switch from amphiphilic to oil-like structures." Phys. Rev. Letts. 95: 218101-1-218101-4 (2005) (publication date: Nov. 15, 2005).

Poteau, S., et al., "Influence of pH on Stability and Dynamic Properties of Asphaltenes and Other Amphiphilic Molecules at the Oil-Water Interface." Energy & Fuels 19: 1337-1341 (2005), (Publ. on Web Mar. 18, 2005).

Schmittel, M., et al., "N,N'-Dimethyl-2,3-dialkylpyrazinium salts as redox-switchable surfactants? Redox, spectral, EPR and surfactant properties." Chem. Comm. 5650-5652 (2005), (Oct. 20, 2005).

Texter J. (editor) Chapter 2 by Holmberg, K., "Cleavable Surfactants." in Reactions and synthesis in surfactant systems: p. 45-58 (2001).

English translation of First Chinese Office Action dated Oct. 18, 2010 for CN Application No. 200680046495.5.

English translation of Second Chinese Office Action dated Jan. 17, 2012 for CN Application No. 200680046495.5.

* cited by examiner

– 1 –
REVERSIBLY SWITCHABLE SURFACTANTS AND METHODS OF USE THEREOF

This application claims the benefit under 35 U.S.C. s. 119 (e) of provisional patent application Ser. No. 60/736,507 filed on Nov. 15, 2005 and Ser. No. 60/736,840, filed on Nov. 16, 2005 the contents of which are hereby incorporated by reference in their entirety.

FIELD OF THE INVENTION

The field of the invention is surfactants, and specifically surfactants that can be reversibly converted to a non-surfactant form.

BACKGROUND OF THE INVENTION

In some chemical and industrial processes it is desirable to create a stable emulsion of two immiscible liquids (e.g., water and oil). For example, in the field of oil drilling it is useful to force water into an underground space. In order to maximize the amount of oil recovered by this technique, surfactants are used and a stable emulsion is obtained. A surfactant is a molecule that has two portions: one portion is water-soluble (hydrophilic, lipophobic) while the other portion is oil-soluble (hydrophobic, lipophilic). Due to this property of dual solubility, surfactants are able to stabilize emulsions because they bridge the interface between the oil and the water.

Once placed in an oil and water mixture, a surfactant orients itself so that its water-soluble portion is surrounded by water molecules and its oil-soluble portion is surrounded by oil molecules. The mixture is therefore more likely to remain as an emulsion in the presence of a surfactant than it is to separate into its two distinct layers. Thus traditional surfactants are used to stabilize emulsions by preventing them from separating into distinct layers. Stable emulsions are desired in some industrial processes: however, once an emulsion is produced, it is often difficult to break it down and recover the immiscible liquids.

Surfactants are key to many industrial processes in manufacturing and in the energy industry. The careful design of surfactant molecules can greatly facilitate separation processes and thereby decrease the environmental impact of these processes. However, surfactants themselves may cause environmental damage when released to the environment. Even within industrial processes traditional surfactants may cause, rather than solve, separation problems when they stabilize unbreakable emulsions.

Emulsions that are stabilized by traditional surfactants require steps to break the emulsion down and capture the two distinct layers. In some cases, the process that is used to break down the emulsion irreversibly alters the traditional surfactant chemically and makes it ineffective as a surfactant for a second cycle in the process. Where the traditional surfactant is not altered in the emulsion break down process, the waste aqueous solution must be disposed of in a manner that prevents contamination of the environment by the surfactant. An example of the environmental damage that can be caused by surfactants is the reduction of surface tension in natural bodies of water. Even a small amount of surfactant that is released into natural waters will alter the surface tension of the water such that water bugs and mosquitoes are unable to walk upon it. Presence of certain surfactants in bodies of water is toxic to insects and other aquatic life. The result is a lack food for fish and other higher aquatic life, which can significantly alter the food chain.

Such disadvantages may be eliminated by the design and implementation of degradable surfactants. Degradable surfactants have been developed which are designed to degrade after release into the environment, for example, after prolonged exposure to sunlight. This degradation is slow and does not address the environmental contamination that occurs from the time of release to the time of the degradation.

It is desirable to have compounds that act as a surfactant in one form, but can be chemically altered, by a trigger, into another form which does not have surfactant properties. In some cases, it is desirable that the second form act as a demulsifier. An emulsion containing such a surfactant can be broken into its component layers by applying the appropriate trigger to turn off the surfactant. Some known controllable surfactants have cleavable portions. Thus, the trigger causes the surfactant to irreversibly fall apart into two or more fragments, where none of the fragments fulfill the surfactant role of the original molecule. The term "cleavable" is used to indicate such a molecule that is irreversibly changed into two or more fragments. These cleavable surfactants usually cleave slowly over time, and the triggers to cleave them are typically heat or acid. Cleavable surfactants are not suited to reuse or recycling since the cleaving reaction is irreversible.

Other controllable surfactants are "switchable surfactants". The term "switchable" is used to indicate a molecule that is reversibly changed when a trigger is applied. The switchable surfactant molecule's structure is thus changed to another structure with greatly reduced or even negligible surface activity. In order for the surfactant to be truly switchable, the non-surfactant form of the molecule must be convertible into the surface-active form by the application of another trigger or removal of the first trigger. Examples of known switchable surfactants are those switched "on" (forming the surfactant form) and "off" (forming the non-surfactant form) by triggers such as acid/base cycles, oxidation/reduction cycles, and photochemistry. The applications of these switchable surfactants are limited in some cases because of side reactions caused by the triggering agents. In the case of switchable surfactants that are used to stabilize emulsions, a photochemical switch is inefficient since the emulsions are usually cloudy and/or impermeable to light. Although a cloudy solution can be exposed to light, the photochemical reaction will be slow since the reaction will only occur where the light has effectively penetrated the solution. A further limitation of the known switchable surfactants is that a stoichiometric amount of acid/base or oxidizer/reducer is required, which means a stoichiometric amount of waste is produced. In some examples of surfactant use, such waste is toxic and must be cleaned up before it can be safely released into the environment.

There is a need to have a surfactant that can effectively be reversibly converted between on and off forms using a trigger, preferably a non-toxic trigger. Such a surfactant would stabilize an emulsion when "on" and allow an emulsion to separate into its two phases (or promote such separation) when "off". Such a surfactant would be suited for recapture, and reuse.

SUMMARY OF THE INVENTION

In a first aspect, the invention provides a compound which reversibly converts to a salt upon contact with carbon dioxide in the presence of water, the compound having the general formula (1):

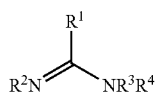
(1)

where
at least one of $R^1$, $R^2$, $R^3$, and $R^4$ is a higher aliphatic and/or siloxyl moiety; and
the rest of $R^1$, $R^2$, $R^3$, and $R^4$ are selected from the group consisting of a $C_1$ to $C_4$ alkyl group, $(SiO)_1$ to $(SiO)_2$, and $C_n(SiO)_m$ where n is a number from 0 to 4 and m is a number from 0 to 2 and $n+m \leq 4$;
where the higher aliphatic and/or siloxyl moiety is a hydrocarbon and/or siloxyl moiety having a chain length of linked atoms corresponding to that of $C_{11}$ to $C_{25}$ which may be substituted or unsubstituted, and may optionally contain one or more SiO unit, an ether or ester linkage or both.

The compound may be a demulsifier in certain embodiments.

In a second aspect, the invention provides a surfactant which reversibly converts to a non-surfactant upon contact with a gas that contains substantially no carbon dioxide, the surfactant having the general formula (2):

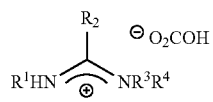
(2)

where
at least one of $R^1$, $R^2$, $R^3$, and $R^4$ is a higher aliphatic and/or siloxyl moiety; and
the rest of $R^1$, $R^2$, $R^3$, and $R^4$ are selected from the group consisting of a $C_1$ to $C_4$ alkyl group, $(SiO)_1$ to $(SiO)_2$, and $C_n(SiO)_m$ where n is a number from 0 to 4 and m is a number from 0 to 2 and $n+m \leq 4$;
where the higher aliphatic and/or siloxyl moiety is a hydrocarbon and/or siloxyl moiety having a chain length of linked atoms corresponding to that of $C_5$ to $C_{25}$ which may be substituted or unsubstituted, and may optionally contain one or more SiO unit, an ether or ester linkage or both.

In a third aspect, the invention provides a surfactant which reversibly converts to a non-surfactant upon contact with a gas that contains substantially no carbon dioxide, the surfactant having the general formula (3):

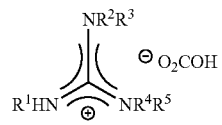
(3)

where
at least one of $R^1$, $R^2$, $R^3$, and $R^4$ is a higher aliphatic and/or siloxyl moiety; and
the rest of $R^1$, $R^2$, $R^3$, and $R^4$ are selected from the group consisting of a $C_1$ to $C_4$ alkyl group, $(SiO)_1$ to $(SiO)_2$, and $C_n(SiO)_m$ where n is a number from 0 to 4 and m is a number from 0 to 2 and $n+m \leq 4$;
where the higher aliphatic and/or siloxyl moiety is a hydrocarbon and/or siloxyl moiety having a chain length of linked atoms corresponding to that of $C_5$ to $C_{25}$ which may be substituted or unsubstituted, and may optionally contain one or more SiO unit, an ether or ester linkage or both.

In a fourth aspect, the invention provides a method for stabilizing an emulsion of two immiscible liquids or of a liquid and a solid comprising: combining said two immiscible liquids or said liquid and solid; adding a compound of the first aspect to one of the liquids or to the mixture; exposing the mixture to carbon dioxide in the presence of water to convert the compound to a salt; and agitating the mixture to form a stable emulsion.

In a fifth aspect, the invention provides a method for stabilizing an emulsion of two immiscible liquids or of a liquid and a solid comprising: combining said two immiscible liquids or said liquid and solid; adding to one of the liquids or to the mixture a surfactant of the second or third aspects or the neutral form of said surfactant; where the neutral form of said surfactant has been added in the prior step, exposing the mixture to carbon dioxide in the presence of water to convert said neutral form to the corresponding said surfactant; and agitating the mixture to form a stable emulsion.

In a sixth aspect, the invention provides a method for separating two immiscible liquids or a liquid and a solid from an emulsion which contains a surfactant of the second or third aspects, comprising: exposing the emulsion to a gas that contains substantially no carbon dioxide to liberate carbon dioxide and convert the surfactant to a non-surfactant; wherein subsequent separation of said two immiscible liquids or said liquid and solid occurs. The gas may be selected from the group consisting of nitrogen, argon, and air that has insufficient carbon dioxide to turn on said surfactant or maintain it in surfactant form.

In a seventh aspect, the invention provides a method for separating two immiscible liquids or a liquid and a solid from an emulsion which contains a surfactant of the second or third aspects, comprising: heating the emulsion to liberate carbon dioxide and convert the surfactant to a non-surfactant; wherein subsequent separation of said two immiscible liquids or said liquid and solid occurs.

In an eighth aspect, the invention provides a compound which reversibly converts to a salt upon contact with (i) gas that liberates hydrogen ions in the presence of water and (ii) water, the compound having the general formula (1):

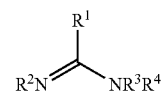
(1)

where
at least one of $R^1$, $R^2$, $R^3$, and $R^4$ is selected from the group consisting of higher aliphatic moiety, higher siloxyl moiety, higher aliphatic/siloxyl moiety, aliphatic/aryl moiety, siloxyl/aryl moiety, and aliphatic/siloxyl/aryl moiety; and
the rest of $R^1$, $R^2$, $R^3$, and $R^4$ are selected from the group consisting of a $C_1$ to $C_4$ aliphatic group, a $(SiO)_1$ to $(SiO)_2$ group, and a $C_n(SiO)_m$ group where n is a number from 0 to 4 and m is a number from 0 to 2 and $n+m \leq 4$;
where a said higher aliphatic and/or siloxyl moiety is a hydrocarbon and/or siloxyl moiety having a chain length of linked atoms corresponding to that of $C_{11}$ to $C_{25}$ which may be substituted or unsubstituted, and may optionally contain one or more SiO unit, an ether or ester linkage or both.

The compound may be a demulsifier in certain embodiments.

In a ninth aspect, the invention provides a surfactant which reversibly converts to a non-surfactant upon heating and/or contact with a flushing gas, the surfactant having the general formula (4):

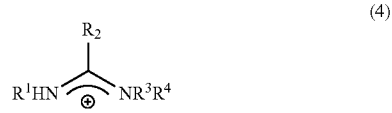
(4)

where
at least one of $R^1$, $R^2$, $R^3$, and $R^4$ is selected from the group consisting of higher aliphatic moiety, higher siloxyl moiety, higher aliphatic/siloxyl moiety, aliphatic/aryl moiety, siloxyl/aryl moiety, and aliphatic/siloxyl/aryl moiety; and
the rest of $R^1$, $R^2$, $R^3$, and $R^4$ are selected from the group consisting of a $C_1$ to $C_4$ aliphatic group, a $(SiO)_1$ to $(SiO)_2$ group, and a $C_n(SiO)_m$ group where n is a number from 0 to 4 and m is a number from 0 to 2 and $n+m \leq 4$;
where a said higher aliphatic and/or siloxyl moiety is a hydrocarbon and/or siloxyl moiety having a chain length of linked atoms corresponding to that of $C_5$ to $C_{25}$ which may be substituted or unsubstituted, and may optionally contain one or more SiO unit, an ether or ester linkage or both.

In a tenth aspect, the invention provides a surfactant which reversibly converts to a non-surfactant upon heating and/or contact with a flushing gas, the surfactant having the general formula (5):

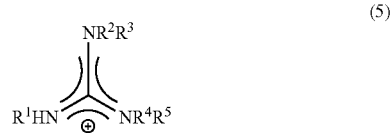
(5)

where
at least one of $R^1$, $R^2$, $R^3$, $R^4$ and $R^5$ is selected from the group consisting of higher aliphatic moiety, higher siloxyl moiety, higher aliphatic/siloxyl moiety, aliphatic/aryl moiety, siloxyl/aryl moiety, and aliphatic/siloxyl/aryl moiety;
and the rest of $R^1$, $R^2$, $R^3$, $R^4$ and $R^5$ are selected from the group consisting of a $C_1$ to $C_4$ aliphatic group, a $(SiO)_1$ to $(SiO)_2$ group, and a $C_n(SiO)_m$ group where n is a number from 0 to 4 and m is a number from 0 to 2 and $n+m \leq 4$;
where a said higher aliphatic and/or siloxyl moiety is a hydrocarbon and/or siloxyl moiety having a chain length of linked atoms corresponding to that of $C_5$ to $C_{25}$ which may be substituted or unsubstituted, and may optionally contain one or more SiO unit, an ether or ester linkage or both.

In an eleventh aspect, the invention provides a method for stabilizing an emulsion of two immiscible liquids or of a liquid and a solid comprising: combining said two immiscible liquids or said liquid and solid; adding a compound of the eighth aspect to one of the liquids or to the mixture; exposing the mixture to a gas that liberates hydrogen ions so that the compound is converted to a salt; and agitating the mixture to form a stable emulsion. In some embodiments, said gas liberates hydrogen ions in the presence of water and water is present in the mixture.

In a twelfth aspect, the invention provides a method for stabilizing an emulsion of two immiscible liquids or of a liquid and a solid comprising: combining said two immiscible liquids or said liquid and solid; adding to one of the liquids or to the mixture a surfactant of the ninth or tenth aspects or the neutral form of said surfactant; where the neutral form of said surfactant has been added in the prior step, exposing the mixture to a gas that liberates hydrogen ions so that the neutral form is converted to the corresponding said surfactant; and agitating the mixture to form a stable emulsion. In some embodiments, said gas liberates hydrogen ions in the presence of water and water is present in the mixture.

In a thirteenth aspect, the invention provides a method for separating two immiscible liquids or a liquid and a solid from an emulsion which contains a surfactant of the ninth or tenth aspects, comprising: exposing the emulsion to a flushing gas so that the surfactant is converted to a non-surfactant; wherein subsequent separation of said two immiscible liquids or said liquid and solid occurs. In some embodiments, said flushing gas is selected from the group consisting of nitrogen, argon, and air that has insufficient carbon dioxide to turn on said surfactant or maintain it in surfactant form.

In a fourteenth aspect, the invention a method for separating two immiscible liquids or a liquid and a solid from an emulsion which contains a surfactant of the ninth or tenth aspects, comprising: heating the emulsion so that the surfactant is converted to a non-surfactant; wherein subsequent separation of said two immiscible liquids or said liquid and solid occurs.

In a fifteenth aspect, the invention provides a method of emulsion polymerization comprising the steps of: combining a monomer, water, a surfactant of the ninth or tenth aspects, and a polymerization initiator; agitating so that an emulsion is created; exposing the emulsion to a flushing gas so that the surfactant is converted to a non-surfactant; and isolating and collecting polymer.

BRIEF DESCRIPTION OF THE DRAWINGS

FIG. 1C shows the syntheses of APSS molecules N'-hexadecyl-N,N-dimethylacetamidine 1a and N'-hexadecyl-N,N-dimethylacetamidinium bicarbonate 2a.

DETAILED DESCRIPTION OF THE INVENTION

Figure 1A:
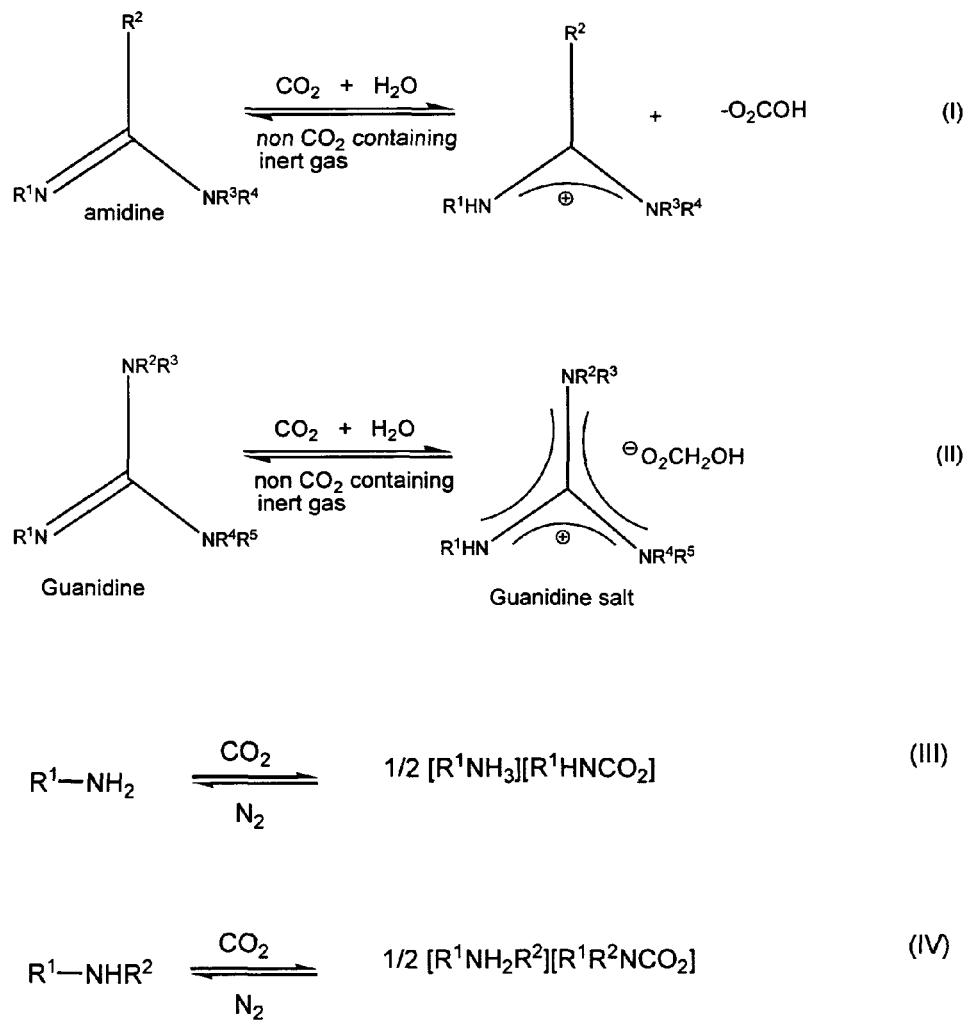
FIG. 1A depicts four schemes in which APSS molecule structures are shown in their non-surfactant (left) and surfactant (right) forms. The first scheme shows the conversion between amidine and amidinium bicarbonate according to the invention. The second scheme shows the conversion between guanidine and guanidinium bicarbonate according to the invention. The third scheme shows the conversion between primary long-chain amine and carbamate salt in which both anion and cation contain a long hydrophobic chain, according to the invention. The fourth scheme shows the conversion between secondary long-chain amine and carbamate salt in which both anion and cation contain a long hydrophobic chain.

As used herein, "aliphatic" refers to hydrocarbon moieties that are straight chain, branched or cyclic, may be alkyl, alkenyl or alkynyl, and may be substituted or unsubstituted. "Short chain aliphatic" or "lower aliphatic" refers to $C_1$ to $C_4$ aliphatic. "Long chain aliphatic" or "higher aliphatic" refers to $C_5$ to $C_{25}$ aliphatic.

As used herein, a "siloxyl" group or chain includes {Si(aliphatic)$_2$-O} units, {Si(aryl)$_2$-O} units, {Si(aliphatic)(aryl)-O} units or combinations thereof. A preferred siloxyl group has {Si(CH$_3$)$_2$—O} units. "Short chain", "long chain", "higher siloxyl" and "lower siloxyl" refer to the same numbers of SiO units as discussed for C units above.

Conveniently, in some discussions hereinbelow, the term "aliphatic/siloxyl" is used as shorthand to encompass "aliphatic" and/or "siloxyl".

As used herein, "heteroatom" refers to non-hydrogen and non-carbon atoms, such as, for example, O, S, and N.

As used herein, an "emulsion" is a heterogeneous system consisting of at least one immiscible liquid dispersed in another in the form of small droplets.

As used herein, the term "wet" in reference to a chemical (e.g., acetonitrile, diethyl ether) means that no techniques were employed to remove water from the chemical.

As used herein, "amidine" refers to a molecule with a structure $R^1N=C(R^2)$—$NR^3R^4$ where $R^1$ through $R^4$ are hydrogen, aliphatic, aryl, siloxyl or combinations thereof. As discussed below, in most embodiments of the present invention, $R^1$ through $R^4$ are aliphatic, aryl, siloxyl, aliphatic/siloxyl, aliphatic/aryl, siloxyl/aryl, or aliphatic/siloxyl/aryl. In those embodiments where any of $R^1$ through $R^4$ is not aliphatic, aryl, siloxyl or a combination thereof, a preferred amidine is $R^1N=CH$—$NR^3R^4$ (i.e., $R^2$ is replaced by H). For purposes of the invention, at least one of $R^1$ through $R^4$ is long chain or higher aliphatic or siloxyl (preferably $C_6$ or equivalent (SiO) length or greater, still more preferably, $C_8$ or equivalent (SiO) length or greater), or another hydrophobic moiety such as, for example, a long chain that is a combination of hydrocarbon units and siloxyl units (with similar length preferences), or long chain aliphatic/aryl. As used herein, the bicarbonate salt of such amidine is termed the "amidinium bicarbonate". Similar nomenclature applies to other salts.

As used herein, "guanidine" refers to a molecule with a structure $R^1N=C(NR^2R^3)(NR^4R^5)$ where $R^1$ through $R^5$ are hydrogen, aliphatic, aryl, siloxyl or combinations thereof. As discussed below, in most embodiments of the present invention where guanidine is a switchable surfactant, $R^1$ through $R^5$ are aliphatic, aryl, siloxyl, aliphatic/siloxyl, aryl/aliphatic, aryl/siloxyl or aliphatic/aryl/siloxyl. For purposes of the invention, at least one of $R^1$ through $R^5$ is long chain or higher aliphatic or siloxyl, or another hydrophobic moiety such as, for example, a long chain that is a combination of hydrocarbon and siloxyl units, or long chain aliphatic/aryl. As above, a longer chain, having at least 6 hydrocarbon units (or equivalent SiO length) is preferred, and at least 8 hydrocarbon units (or equivalent SiO length) is more preferred. As used herein, the bicarbonate salt of guanidine is termed the "guanidinium bicarbonate". Similar nomenclature applies to other salts.

As used herein, "gases that liberate hydrogen ions" fall into two groups. Group (i) includes gases that liberate hydrogen ions in the presence of a base, for example, HCN and HCl (water may be present, but is not required). Group (ii) includes gases that when dissolved in water react with water to liberate hydrogen ions, for example, $CO_2$, $NO_2$, $SO_2$, $SO_3$, $CS_2$ and COS. For example, $CO_2$ in water will produce $HCO_3^-$ (bicarbonate ion) and $CO_3^{2-}$ (carbonate ion) and hydrogen counterions, with bicarbonate being the predominant species. One skilled in the art will recognize that the gases of group (ii) will liberate a smaller amount of hydrogen ions in water in the absence of a base, and will liberate a larger amount of hydrogen ions in water in the presence of a base.

As used herein, "flushing gases" are gases that do not liberate hydrogen ions in the presence of a base, and that when dissolved in water do not react with water to liberate hydrogen ions even in the presence of a base. Thus, this term is used to distinguish such gases from gases that liberate hydrogen ions as discussed above, and there is no intended implication from the word "flushing" that movement is absolutely required. As described in detail below, according to the invention, a flushing gas is used to expel a gas that liberates hydrogen ions from a mixture. Examples of flushing gases are $N_2$, air, air that has had its carbon dioxide component substantially removed, argon, oxygen, He, $H_2$, $N_2O$, CO, ethane, ethylene, propane, methane, dimethylether, tetrafluoroethylene, and combinations thereof.

As used herein, "air that has had its carbon dioxide component substantially removed" means that the air has been depleted of carbon dioxide such that the remaining amount is insufficient to turn "on" a surfactant of the invention. That is, the carbon dioxide level does not have to be reduced to zero.

The invention provides a switchable surfactant that can be reversibly and readily switched between surfactant ("on") and non-surfactant ("off") forms by applying a trigger. The surfactant includes a cationic moiety and can conveniently be isolated as a salt with an anionic counterion such as, for example, a bicarbonate ion. A non-surfactant means a compound with little or no surface activity. Exemplary switchable surfactants are depicted in FIG. 1 and discussed below.

A gas that liberates hydrogen ions is employed as a trigger to turn "on" a switchable surfactant of the invention. Preferred gases that liberate hydrogen ions are those wherein the surfactant switches to its "off" form when the same gas is expelled from the environment. $CO_2$ is particularly preferred. Hydrogen ions produced from dissolving $CO_2$ in water protonate the "off" form of a switchable surfactant, thus turning it "on". In such solution, the counterion for the positively charged surfactant is predominantly bicarbonate. However, some carbonate ions are also present in solution and the possibility that, for example, two surfactant molecules, each with a single positive charge, associate with a carbonate counterion is not excluded. When $CO_2$ is expelled from the solution, the surfactant is deprotonated and thus converted to its "off" form.

Of group (ii) gases that liberate hydrogen ions, $CS_2$ and COS are expected to behave similarly to $CO_2$ to form surfactants that are reversibly switchable. However, it is expected that the reverse reaction, i.e., from "on" surfactant to "off", may not proceed as easily to completion as with $CO_2$. In some embodiments of the invention, alternative gases that liberate hydrogen ions are used instead of $CO_2$, or in combination with $CO_2$, or in combination with each other. Alternative gases that liberate hydrogen ions are less preferred because of the added costs of supplying them and recapturing them, if recapturing is appropriate. However, in some applications one or more such alternative gases may be readily available and therefore add little to no extra cost. Group (i) gases HCN and HCl are less preferred triggers because of their toxicity and because reversibility would likely require a strong base.

A gas that liberates hydrogen ions may be expelled from a solution including surfactant by simple heating. Alternatively and conveniently, a flushing gas may be employed to expel a gas that liberates hydrogen ions (e.g., group (ii) gas) from a solution including surfactant. This shifts the equilibrium from "on" form to "off" form.

Preferred flushing gases are $N_2$, air, air that has had its carbon dioxide component substantially removed, and argon. Less preferred flushing gases are those gases that are costly to supply them and/or to recapture, where appropriate. However, in some applications one or more flushing gases may be readily available and therefore add little to no extra cost. In certain cases, flushing gases are less preferred because of their toxicity, e.g., carbon monoxide.

Air is a particularly preferred choice as a flushing gas according to the invention, where the $CO_2$ level of the air (today commonly 380 ppm) is sufficiently low that an "on" surfactant in not maintained in "on" form. Untreated air is preferred because it is both inexpensive and environmentally sound. In some situations, however, it may be desirable to employ air that has had its carbon dioxide component substantially removed as a flushing gas. By reducing the amount of $CO_2$ in the flushing gas, potentially less surfactant may be employed. Alternatively, some environments may have air with a high $CO_2$ content, and such flushing gas would not achieve complete switching of "on" surfactant to "off". Thus, it may be desirable to treat such air to remove enough of its $CO_2$ for ready switching off of the surfactant.

The invention also provides a method for separating two immiscible liquids using a reversibly switchable surfactant. The invention further provides a method for maintaining an emulsion using a reversibly switchable surfactant. The surfactant may then be turned off and the immiscible liquids separated.

In certain embodiments of the invention, two immiscible liquids are (1) water or an aqueous solution and (2) a water-immiscible liquid such as a solvent, a reagent, a monomer, an oil, a hydrocarbon, a halocarbon, or a hydrohalocarbon. The water-immiscible liquid could be pure or a mixture. Solvents include, for example and without limitation, alkanes, ethers, amines, esters, aromatics, higher alcohols, and combinations thereof. Monomers include, for example and without limitation, styrene, chloroprene, butadiene, acrylonitrile, tetrafluoroethylene, methylmethacrylate, vinylacetate, isoprene, and combinations thereof. Oils include, for example and without limitation, crude oil, bitumen, refined mineral oils, vegetable oils, seed oils (such as soybean oil and canola oil), fish and whale oils, animal-derived oils, and combinations thereof. Halocarbons include, for example and without limitation, perfluorohexane, carbon tetrachloride, and hexafluorobenzene. Hydrohalocarbons include, for example and without limitation, (trifluoromethyl)benzene, chlorobenzene, chloroform, chlorodibromomethane, partially fluorinated alkanes, and combinations thereof. A water-immiscible liquid could be a gas at standard temperature and pressure but a liquid or supercritical fluid at the conditions of the application. (Supercritical fluids, while not technically liquids, are intended to be included when liquids are discussed.)

In other embodiments of the invention, two immiscible liquids are a more polar liquid and a less polar liquid. Polar compounds have more hydrogen bonding and/or greater dipole moments and/or charge separation. They include, for example, solvents, reagents and monomers such as alcohols (e.g., methanol, ethylene glycol, glycerol, vinyl alcohols), carboxylic acids (e.g., acrylic acid, methacrylic acid, acetic acid, maleic acid), nitriles (e.g., acetonitrile), amides (e.g., acrylamide, dimethylformamide), sulfoxides (e.g., dimethylsulfoxide), carbonates (e.g., propyl carbonate), sulfones (e.g., dimethylsulfone), ionic liquids, and other highly polar liquids, e.g., hexamethylphosphorus triamide, nitromethane, 1-methylpyrrolidin-2-one, sulfolane, and tetramethylurea. Less polar compounds have less hydrogen bonding and/or lesser dipole moments and/or less charge separation. Less polar liquids include solvents, reagents, monomers, oils, hydrocarbons, halocarbons, and hydrohalocarbons as described previously. These could be pure liquids, mixtures or solutions.

In other embodiments of the invention, two immiscible liquids are two immiscible aqueous solutions, for example, an aqueous solution of polyethylene glycol and an aqueous solution of a salt.

In some embodiments, a switchable surfactant of the invention can be used with a mixture of a liquid and a solid, such as is demonstrated in Example 6.

Figure 1B:
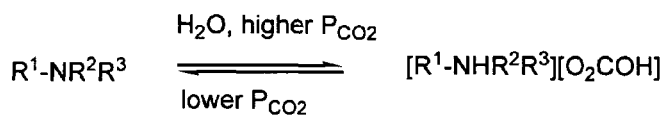
FIG. 1B depicts a scheme in which HPSS molecule structures are shown in their non-surfactant (left) and surfactant (right) forms.
Figure 1C:
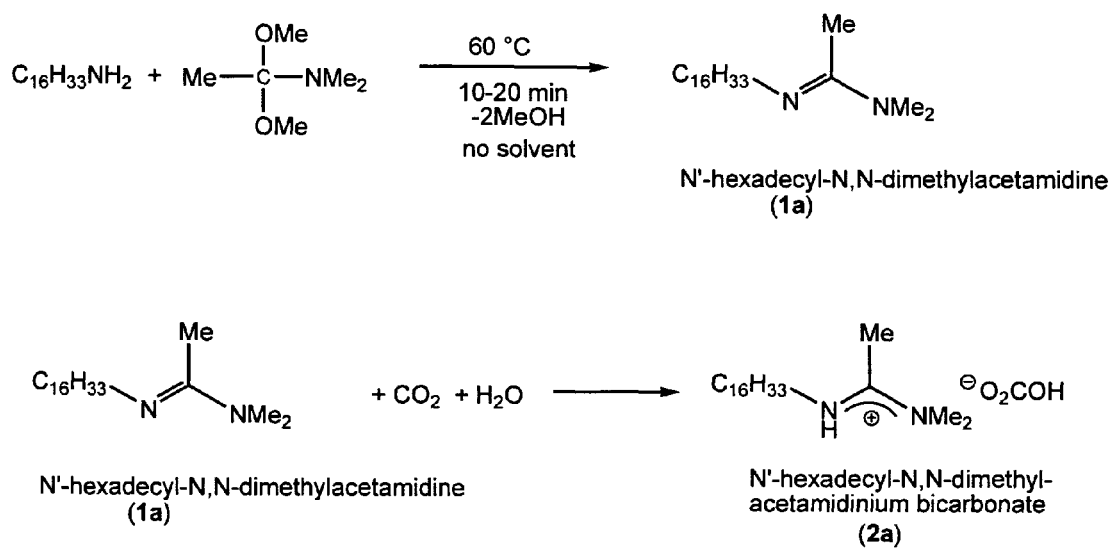

Referring to FIG. 1A, four schemes are provided for atmospheric pressure switchable surfactants (APSS) according to the invention. Referring to FIG. 1B, a scheme is provided for high pressure-switchable surfactants (HPSS) according to the invention. FIG. 1C shows the syntheses of APSS molecules N'-hexadecyl-N,N-dimethylacetamidine 1a and N'-hexadecyl-N,N-dimethylacetamidinium bicarbonate 2a.

Conveniently, APSS and HPSS of the invention will now be discussed where $CO_2$ is employed as an exemplary (non-limiting) trigger (gas that liberates hydrogen ions). Both APSS and HPSS use $CO_2$ as the trigger for switching on the surface activity, but differ in the pressure of $CO_2$ required and in the method for switching off the surface activity. The APSS molecules are able to react with $CO_2$ at 1 atm or less to produce the surfactant form. They are conveniently switched off by heating and/or by flushing the system with a flushing gas (e.g., $N_2$, argon) that is substantially free of any gas that liberates hydrogen ions (e.g., $CO_2$) to remove the $CO_2$ from the system. Other methods of expelling $CO_2$ from the system are, for example, applying a vacuum, applying flushing gas in countercurrent flow, pouring the system into an environment of flushing gas, and exposing the system to a flushing gas, for example, spreading a thin layer on a surface in an environment of flushing gas (e.g., applying paint which is either a mixture of immiscible liquids, or a mixture of a solid and a liquid such as latex paint, to a wall in air).

Preferred flushing gases include, for example, $N_2$, air that has insufficient carbon dioxide to turn on said surfactant or maintain it in surfactant form, air with the carbon dioxide component removed, argon, and combinations thereof. HPSS molecules require a greater pressure of $CO_2$ in order to become surfactants and are switched off by a reduction in $CO_2$ pressure to about 1 atm. HPSS embodiments may be more time efficient in switching off processes.

As shown in FIG. 1A, APSS molecules include amidines, guanidines and primary and secondary amines, each with higher aliphatic/siloxyl portion(s) as discussed below. Such amidines or guanidines are preferably peralkylated. The term "peralkylated" as used in this context means that the amidine or guanidine contains no N—H bonds. This lack of N—H groups is to avoid irreversible reactions with carbon dioxide and to minimize hydrogen bonding interactions between the "off" form and water. As discussed below, preferred compounds of the invention do not contain reactive moieties such as, for example, halo groups. Other compounds of the invention do not contain reactive moieties such as unsaturated bonds other than the C=N of the amidine or guanidine.

Compounds of the invention have at least one hydrophobic group that is soluble in a non-aqueous phase, such as, for example, a higher aliphatic (preferably $C_6$-$C_{25}$, still more preferably $C_8$-$C_{25}$) group, aryl group, or higher siloxyl, aliphatic/siloxyl, aliphatic/aryl, siloxyl/aryl, or aliphatic/siloxyl/aryl group (with similar length preferences), and a group that is switchable and in the surfactant form is soluble in an aqueous phase. The purpose of the higher aliphatic and/or siloxyl group (or equivalent group comprising aryl) is to provide good solubility in the non-aqueous or hydrophobic phase. Accordingly, a compound having a long chain group including an ether moiety is also encompassed by the invention, as this "higher aliphatic/siloxyl group" still provides solubility in the non-aqueous or hydrophobic phase. In certain preferred embodiments, the higher aliphatic/siloxyl group is higher alkyl, preferably having at least 6 hydrocarbon units, still more preferably at least 8 hydrocarbon units. Here, alkyl is preferred because alkenyl and alkynyl groups may be undesirably reactive in some applications. The higher aliphatic/siloxyl group may be substituted with one or more moieties such as, for example, aryl, $Si(alkyl)_3$, phenyl, heteroaryl where the heteroatom is an oxygen, and alkoxy. Reactive substituents such as halo, amine, and —$N(alkyl)_2$ are not preferred, though, for example, a tertiary amino group is less reactive and could be a substituent in some embodiments. Hydrophilic substituents on the higher aliphatic/siloxyl group, such as, for example, OH, SH and COOH are also not preferred.

It is preferred that the compound of the invention have one higher aliphatic/siloxyl group, although it is expected that having two or three higher aliphatic/siloxyl moieties would still enable the compound to function in the intended way. In embodiments of amidines of the invention where there are two higher aliphatic/siloxyl groups, preferably they are $R^1$ and $R^2$, or $R^2$ and $R^3$, or $R^1$ and $R^4$, or $R^3$ and $R^4$. That is, hydrophobic portions of the molecule are sequestered together, and apart from hydrophilic portions of the molecule. Embodiments with three higher aliphatic/siloxyl groups preferably have the higher alkyl groups in the $R^2$, $R^3$ and $R^4$ positions. Similarly, sequestration of higher aliphatic/siloxyl groups applies to guanidine compounds that function as switchable surfactants according to the invention.

The remaining R groups of the compounds of the invention that are not higher aliphatic/siloxyl are hydrogen, lower aliphatic/siloxyl, lower aliphatic/silyl or aryl groups, and are preferably small, non-polar (non-hydrogen bonding) and non-reactive. Examples of such groups include H and lower alkyl ($C_1$ to $C_4$) groups. Preferred examples are $CH_3$, $CH_2CH_3$, $CH(CH_3)_2$, $C(CH_3)$, $Si(CH_3)_3$, and phenyl; a methyl group is particularly preferred. In some embodiments, a compound of the invention has at least one R group that is higher aliphatic (preferably $C_6$-$C_{25}$, more preferably $C_8$-$C_{25}$), aryl, higher siloxyl, aliphatic/siloxyl, aliphatic/aryl, siloxyl/aryl, or aliphatic/siloxyl/aryl (all with similar length preferences), and two of the remaining R groups, taken together with the atoms of the amidine or guanidine to which they are attached, form an unsubstituted or substituted heterocycle having from four to seven atoms in the heterocyclic ring. In other embodiments, the higher aliphatic group itself may participate in forming a ring, so long as the hydrophobicity required for surfactant function is maintained.

The amidine and guanidine switchable surfactants in their "on" forms (cationic forms) have a charged N—H moiety. Whether H is suitable as an R group in the "off" form depends on the particular switchable surfactant, as such N—H may possess undesirable properties in the "off" surfactant. Such potential undesirable properties include (i) interference with the reversibility of the "on"/"off" conversion reaction; and (ii) hydrogen bonding that confers hydrophilicity on the portion of the surfactant that would otherwise be hydrophobic, thereby possibly causing some surfactant property to be present in what otherwise would be the "off" form of the molecule. In contrast, a switchable surfactant based on a primary or secondary amine (see FIG. 1A (III) and (IV)) has an N—H moiety in its "off" form which permits function as APSS.

Figure 4:
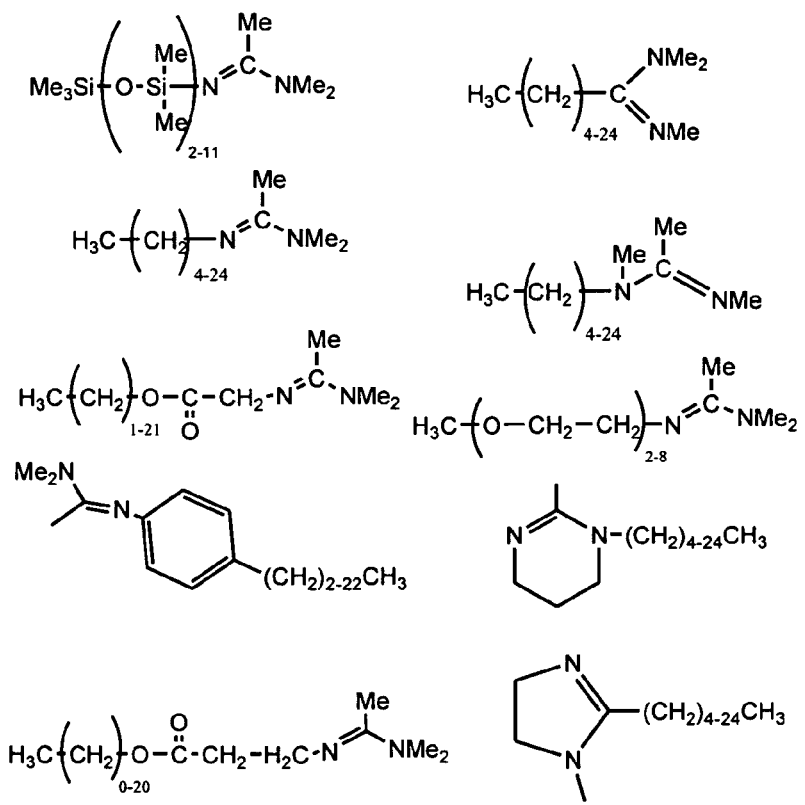
FIG. 4 shows examples of amidines of the invention.

FIG. 4 shows examples of amidines of the invention. Corresponding guanidines that function as switchable surfactants are also encompassed by the invention. Syntheses of amidine compounds of the invention, and demonstration of their properties are described and discussed in the working examples below. In particular, Example 3B sets forth testing of three amidine compounds that differ in length of R group (butyl, hexyl, octyl) with respect to their ability to stabilize an emulsion. Compound N'-butyl-N,N-dimethylacetamidinium bicarbonate (2d) did not function as a switchable surfactant of the invention; compound N'-hexyl-N,N-dimethylacetamidinium bicarbonate (2e) displayed some ability to stabilize an emulsion; and compound N'-octyl-N,N-dimethylacetamidinium bicarbonate (2c) demonstrated good utility as a switchable surfactant. Thus, longer chain length is preferred here. In other studies, 2b (dodecyl R group) was found to exhibit superior properties to 2c (octyl). 2b and 2a (hexadecyl) exhibited equivalent properties.

Figure 9:
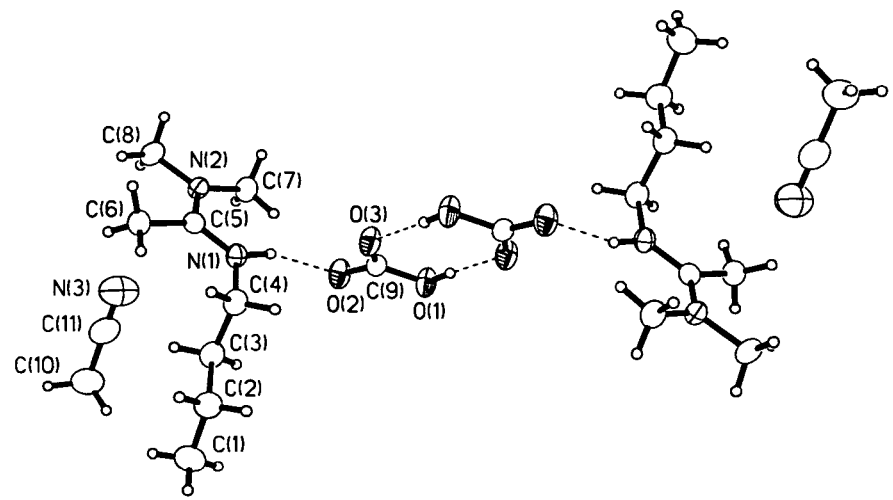
FIG. 9 shows X-ray crystal structure of N'-butyl-N,N-dimethylacetamidinium bicarbonate (2d). Each unit cell contains two N'-butyl-N,N-dimethylacetamidinium cations, two-bicarbonate anions, and two acetonitrile solvent molecules.
Figure 10:
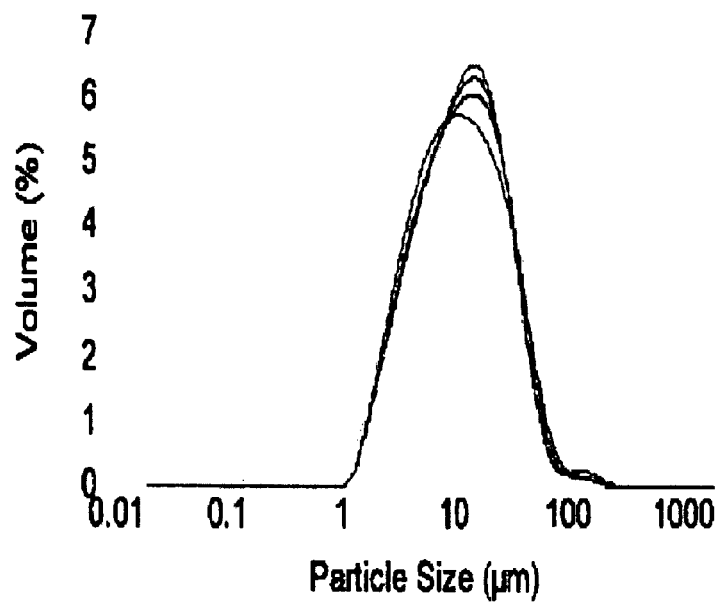
FIG. 10 shows a plot of particle size distribution of polystyrene particles made in the presence of 2b without sonication.
Figure 11:
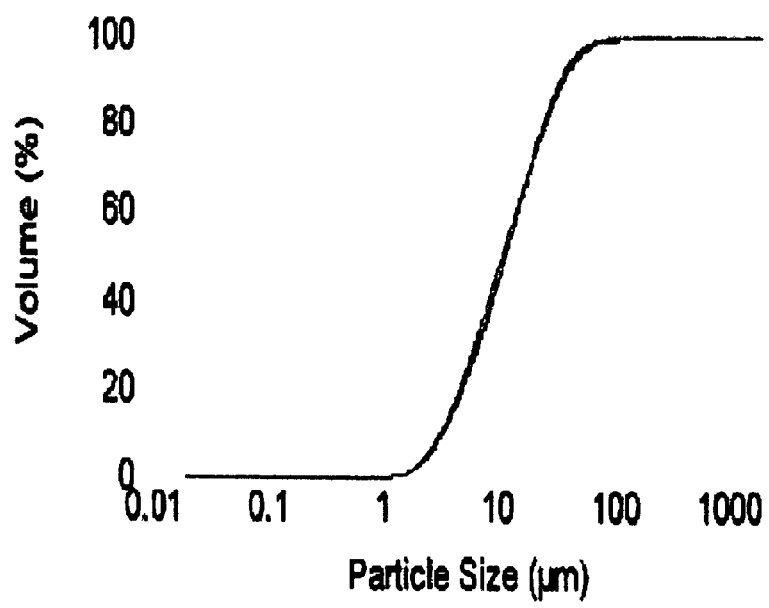
FIG. 11 shows a plot of cumulative particle size distribution of polystyrene particles made in the presence of 2b without sonication.
Figure 12:
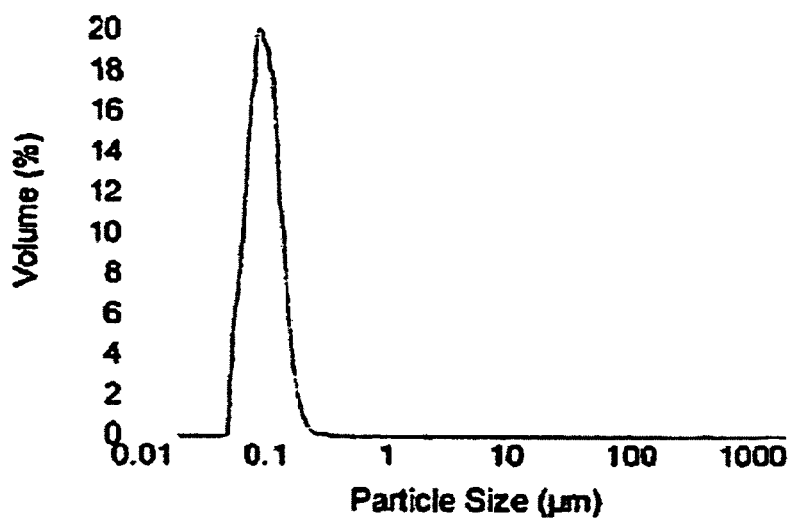
FIG. 12 shows a plot of particle size distribution of polystyrene particles made in the presence of 2b with sonication.
Figure 13:
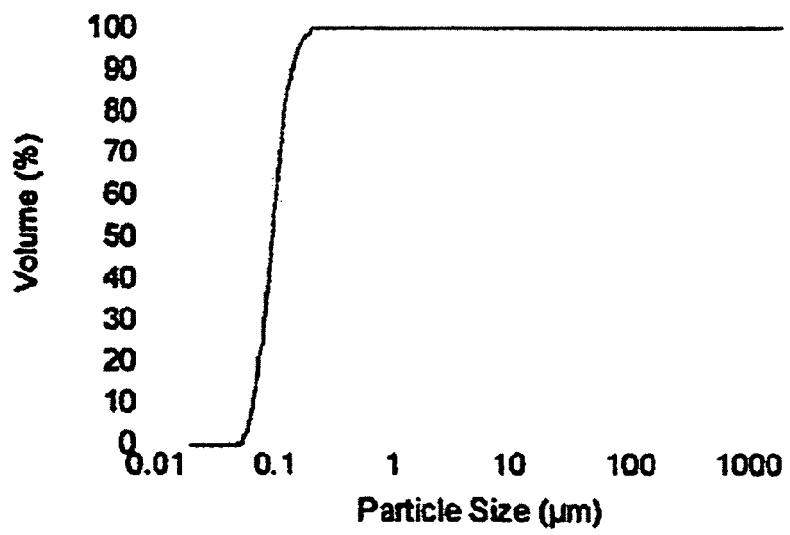
FIG. 13 shows a plot of cumulative particle size distribution of polystyrene particles made in the presence of 2b with sonication.

Notwithstanding the above, the crystal structure obtained for 2d as described in Example 2C and shown in FIG. 9 confirms the products of first reaction scheme set forth in FIG. 1A.

Further emulsion studies are described in Example 7A-D. Of particular interest, amidine compound 2a (N'-hexadecyl-N,N-dimethylacetamidinium bicarbonate) was tested for its ability to stabilize emulsions of different types of light and heavy crude oil with water (see Example 7C and Table 2). As would be appreciated by a person of ordinary skill in the oil industry, crude oils vary greatly in their composition, including percentage composition asphaltene, which substance may act as a surfactant. The results set forth herein support utility of 2a and like compounds of the invention for applications in the oil industry, as discussed below.

Example 7D sets forth exemplary studies on droplet size in an emulsion, and provides guidance in regard to factors involved in minimization of droplet size. Where persistence of an emulsion is desirable (e.g., when an oil/water emulsion is being pumped in a pipeline), minimal droplet size promotes greater stability.

Example 8 describes critical micelle concentration determination for certain amidines of the invention. Charge of an ionic surfactant molecule enables it to confer electrical conductivity on its solution. At a critical micelle concentration (CMC), surfactant molecules begin to aggregate into micelles, whose mobility differs significantly from that of single ions; thus, when electrical conductivity data are plotted against surfactant concentrations, there is an abrupt change in specific conductivity at the CMC (Patist, A., *Hand Book of Applied Surface and Colloid Chemistry*, Vol. 2 (Ed.: K. Holmberg), John Wiley & Sons, New York, 2002; Schultz, P. C.; Clausse, D.; *J. Chem. Ed.* 2003, 80, 1053). CMC is an indicator of surfactant efficiency (D. Myers, *Surfactant Science and Technology*, 3$^{rd}$ ed., John Wiley & Sons Inc.: New York, U.S.A., 2006). A lower CMC indicates less surfactant is needed to saturate interfaces and form micelles. The data set forth in Table 5 of Example 8, where CMC values for switchable surfactants of the invention are presented side-by-side with textbook values for commercially available surfactants, indicate that the compounds of the invention have significant utility, as demonstrated by their comparatively low CMC values.

Two guanidine compounds have been synthesized but have not been shown to have switchable surfactant properties. For the first such compound, $R^1$ was hexadecyl and the remaining R groups were methyl. However, during its separation, this compound formed an emulsion with organic solvent and water so work on it has not continued. For the second such compound, one of $R^2$ to $R^5$ was octyl and the remaining R groups were H. This compound did not perform well as a surfactant when tested with a diethyl ether/water mixture or a hexadecane/water mixture (though the aqueous phase was observed to be somewhat cloudy). Thus, amidine compounds described herein are currently preferred as switchable surfactants, though it is expected that some guanidine compounds having structures described herein will also be useful switchable surfactants.

In certain embodiments, the invention provides a cleavable switchable surfactant including a sensitive functional group that can be cleaved by exposure of the surfactant to acid, base, ozone, or light.

In certain preferred embodiments of the APSS molecules, at least one aliphatic/siloxyl group includes a functionality such as an ester moiety, which allows the surfactant to be readily cleaved when in the environment. It should be understood that the non-carbonyl oxygen of the ester moiety should not be adjacent to nitrogen of the amidine or guanidine, to minimize undesirable reactivity. However, the ester moiety should not be spaced too far from the amidine or guanidine such that after the cleavage the amidine or guanidine is still able to act as a surfactant, e.g., upon reaction with an acid. Rather, the ester moiety may be in either orientation (—O—C(O)amidine or C(O)—O-amidine) and is spaced 1-3 carbons from the nitrogen.

FIG. 1B shows an HPSS molecule ($R^1$—$NR^2R^3$), where $R^1$ is higher aliphatic/siloxyl as defined above for APSS molecules. As a tertiary amine, the depicted HPSS molecule is somewhat less basic than the APSS molecules. This implies that an HPSS molecule requires higher $CO_2$ pressures to react and form the salt form (surfactant). Typical HPSS molecules are nitrogen-containing bases with basicities that are below those of the APSS molecules, but that are still sufficient to stabilize bicarbonate salts at elevated pressure. For example, alkyldimethylamines where the alkyl group is a long hydrophobic chain are expected to have sufficient basicity. However, in initial HPSS testing of a tertiary amine where $R^1$ is dodecyl and $R^2$ and $R^3$ are both methyl (N-dodecyl-N,N-dimethylamine), a hexadecane/water emulsion was not stabilized, even in the presence of $CO_2$. This is being retested. It should be understood that the invention further encompasses amidine or guanidine compounds that have low basicities and react with $CO_2$ in the presence of water under high pressure (i.e., are HPSS compounds).

In some embodiments of the invention, HPSS molecules are amidines or guanidines of similar structure to APSS molecules but bearing substituents that withdraw sufficient electron density from the N atoms to make them insufficiently basic to serve as APSS molecules.

Although the requirement for high pressure in generation of an HPSS surfactant can be viewed as a disadvantage, the ability to switch off such a molecule rapidly by reduction of the $CO_2$ pressure may conversely be viewed as an advantage. For these reasons, the HPSS molecules may be particularly suited to EOR (or WAG) applications (discussed below), where elevated $CO_2$ pressure is used.

The invention provides non-surfactant compounds that react with $CO_2$ in the presence of water to generate bicarbonate or carbamate salts which are useful surfactants. One portion of the cation of the bicarbonate salt and both portions of the carbamate salt have a hydrophobic moiety, therefore due to the presence of both a charged portion and a hydrophobic portion, the salts have surface activity. Compounds of the invention may be added to the aqueous layer or the non-aqueous layer prior to mixing, or to the emulsion after mixing.

Gas that liberates hydrogen ions may be provided from any convenient source, for example, a vessel of compressed $CO_{2(g)}$ or as a product of a non-interfering chemical reaction. Flushing gas may be provided from any convenient source, for example, a vessel of compressed flushing gas (e.g., $N_{2(g)}$, air that has insufficient carbon dioxide to turn on said surfactant or maintain it in surfactant form, air which has had its $CO_{2(g)}$ substantially removed, $Ar_{(g)}$) or as a product of a non-interfering chemical reaction. Conveniently, such exposure is achieved by bubbling the gas through the mixture. However, it is important to recognize that heating the mixture is an alternative method of driving off the $CO_2$, and this method of converting the surfactant to non-surfactant is also encompassed by the invention. In certain situations, especially if speed is desired, both bubbling and heat can be employed.

Figure 2:
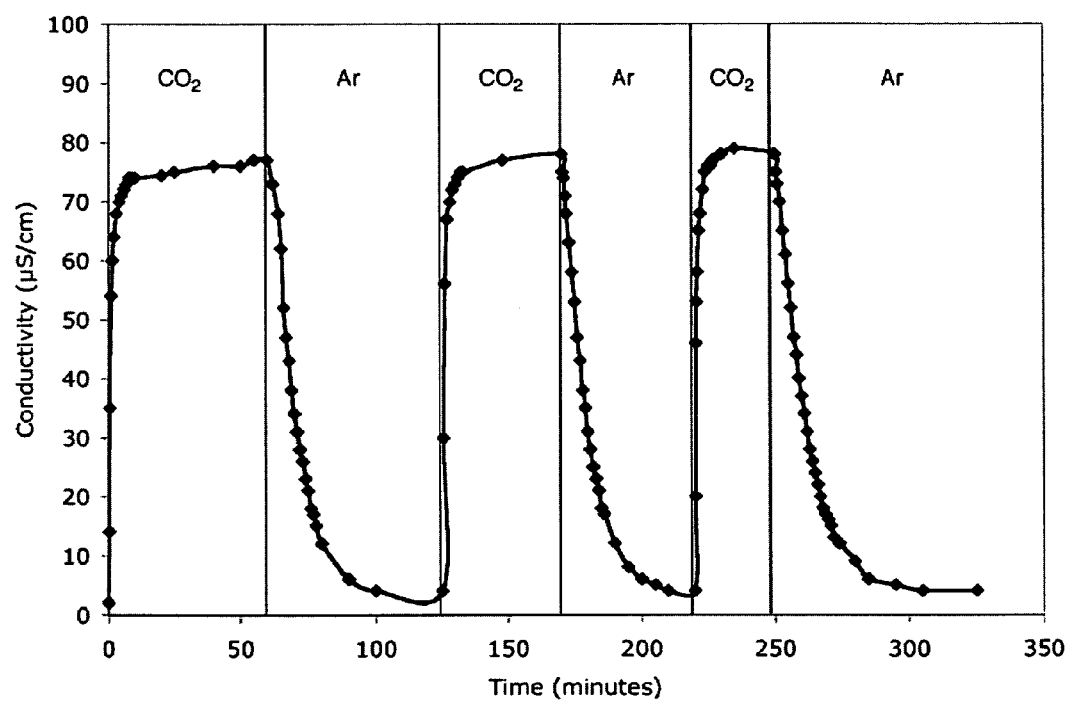
FIG. 2 shows a plot of conductivity of a DMSO solution of 1a at 23° C. as a function of time during three cycles of treatment with $CO_2$ followed by treatment with argon.

Reuse and recycling of surfactants of the invention are convenient, with attendant economic benefits. FIG. 2 shows that the time required to switch between the surfactant and non-surfactant forms according to the invention is short, as exemplified by the switch from 1a to 2a and back. In certain applications, it may be advantageous to turn off the surfactant and then turn it back on again. For example, the surfactant could be turned on to stabilize an emulsion, and turned off to allow for separating and decanting of the hydrophobic and/or hydrophilic layers and/or isolation of a precipitate. In its "off" form, the switchable surfactant will partition into the non-aqueous phase, which can be decanted. The surfactant can be reused by adding fresh aqueous solution and converting the non-surfactant to its surfactant form. The newly formed surfactant will then partition into the aqueous phase.

Example 4 indicates that the amidinium bicarbonate salt 2a can be decomposed and releases $CO_2$ and water between about 50° C. and about 63° C. $CO_2$ loss between room temperature and 100° C. is desirable; therefore the observed temperature of between 50 and 63° C. is within the desired range. If the temperature of decomposition of 2a had been higher than 100° C., it is unlikely that the compound would have released its $CO_2$ even in boiling water; the amidinium bicarbonate salt would have been too stable to be switchable. If the temperature of decomposition had been lower than room temperature, the amidinium bicarbonate salt would not have been stable at room temperature; it would have switched "off" to create the neutral amidine.

If isolation of a switchable surfactant of the invention is desired, it can be isolated in either of its forms by taking advantage of their contrasting solubilities. When the "on" (salt) form is turned off, the switchable surfactant separates from aqueous solution, allowing for its easy recovery. Alternatively, the "on" form precipitates from non-aqueous solution, and is conveniently recovered.

The invention provides a convenient system to control the presence or absence of a surfactant in a mixture such as an emulsion. Thus, it is useful in many industrial applications. In the oil industry, where mixtures of crude oil and water must be extracted from subterranean cavities (water is even pumped into an underground oil reservoir), emulsions can first be stabilized with a surfactant of the invention. Subsequently, the emulsion can be conveniently and readily broken by bubbling the emulsion with an appropriate flushing gas to turn off the surfactant. The use of switchable surfactants in enhanced oil recovery (EOR) could allow for simpler recovery of the emulsified oil, even at the production point. Oil field operations are used to dealing with $CO_2$ as a diluent, and some EOR processes (e.g. the water-alternating-gas or "WAG" process) use water, high pressure $CO_2$, and surfactants together (Schramm, L. L., Ed. *Foams: Fundamentals and Applications in the Oil Industry*; American Chemical Society: Washington, D.C., 1994 and Borchardt, J. K. In Kirk-Othmer Encyclopedia of Chemical Technology; 4th ed.; Kroschwitz, J. I., Howe-Grant, M., Eds.; Wiley: New York, 1996; Vol. 18, p 405). Emulsions in the product oil impede separation, a problem which could be eliminated by a reversibly switchable surfactant.

Reversibly switchable surfactants of the invention are well suited for controlling $CO_2$ hydrate formation in oil field and petroleum transport applications. Also, switchable surfactants are employable for deoiling and demulsification applications. For example, a high HLB reversibly switchable surfactant could be used to break water out of produced oil, and then switched off to avoid downstream problems (toxicity, biodegradability, and emulsification) with the recovered water. For such an application, a surfactant that does not switch on again upon exposure to air is preferred. As discussed herein, the chosen surfactant may conveniently be an APSS molecules. An HPSS surfactant may be also be suitable.

The switchable surfactant system according to the invention can facilitate water/solid separations in mining. In mineral recovery, switchable surfactants may be suitable as flotation reagents which are mineral-specific agents that adsorb to the mineral particles to render them hydrophobic and therefore likely to float upon aeration. Flotation reagents designed on the basis of switchable surfactants could be readily removed from minerals and recycled.

In certain applications, switchable surfactants can be employed in salt rich environments. Studies have been conducted (see Example 10) that indicated that the reversibility of amidine 1a is not affected by the presence of sodium, nor calcium, but that a high concentration of iron salts can inhibit the ability of the surfactant to turn "off". Thus, 1a and like compounds can be employed as switchable surfactants in the presence of $Ca^{2+}$ or $Na^+$ salts. However, they will apparently not be reversible in the presence of a high concentration of $Fe^{3+}$. This result indicates that amidines of the invention can be suitable for extracting metal salts such as $Fe^{3+}$ from aqueous solutions or from matrices into organic solvents or other hydrophobic phases.

The switchable surfactant system of the invention can be employed for extraction of a hydrophobic substance from a mixture or matrix using a combination of water or aqueous solution and surfactant, for example, oil from porous rock, spilled oil from contaminated soil, desirable organic compounds from biological material (plant or animal), ink from paper, dirt from clothing. Analogously, the invention provides a method for extracting a hydrophilic substance from a mixture or matrix using a combination of organic solvent and surfactant, for example, caffeine from coffee, metal salts from soil, salts or polyols (e.g., sugars) from organic mixtures. In each case, the extracted substance can be recovered from solvent by turning off the switchable surfactant.

Switchable surfactants of the invention can be useful as corrosion inhibitors, in oil-sands separation processes, and in cleaning of equipment. Reversibly switching between surfactant and demulsifier has particular utility for the oil industry.

Switchable surfactants of the invention can be useful in water/solvent separations in biphasic chemical reactions. An example is homogeneously-catalyzed reactions in organic/aqueous mixtures. Initially, with the surfactant "switched on", a water-soluble homogeneous catalyst dissolved in water could be used to catalyze reactions such as, for example, hydrogenation or hydroformylation of organic substrates such as olefins in an immiscible organic phase. With appropriate agitation or shear to create an emulsion, the reaction should be fairly rapid due to enhanced mass transfer and contact between the two phases. After the reaction is complete, the surfactant is switched off to break the emulsion, and then the two phases are separated. The surfactant, being at this point a nonpolar organic molecule, will be retained in the organic phase but can be readily precipitated from that solution by being switched back on again. The surfactant can then be recovered by filtration so that it can be reused and will not contaminate the product or waste streams.

Reversibly switchable surfactants can be useful additives in polymerization reactions (see Example 9). A switchable surfactant can be used in an emulsion or microsuspension polymerization of water insoluble polymers. This permits manufacture of very high molecular weight polymers which are recovered from solution by switching off the surfactant, filtering and drying the obtained solid. In general, such high molecular weight polymers are difficult to produce in a solution polymerization process without surfactants because of their tendency to form gels. Switchable surfactants of the invention could protect surfaces of nanoparticles, colloids, latexes, and other particulates during synthesis and use. In the absence of a coating of surfactant, such particles tend to agglomerate. But, in many cases, once the synthesis is complete, the presence of surfactant is no longer desirable. For example, in preparation of supported metal catalysts, complete removal of surfactant is desired, but it is difficult with non-switchable surfactants, since they bind strongly to the surface.

When polymers are prepared by emulsion or microsuspension polymerization, it is preferred that the particle size of the resulting solid polymer be small (i.e., 1 μm), so that (a) the polymer particles will not settle out during transport and/or storage, and (b) high conversion of monomer is obtained. Later, when the polymer is to be isolated from the aqueous suspension, it is preferred that the particle size be larger because that will make isolation of the polymer by settling or filtration easier and more effective. Small particles would either pass entirely through a filter, clog up the filter, or make it necessary to use a very fine and therefore inefficient filter. Accordingly, in such applications, a switchable surfactant of the invention would be "on" to keep particle size small during formation, transport and storage of the (latex) suspension but "off" before and during the isolation of the polymer.

Thus, small particle size and a narrow particle size distribution are desirable, for example, in the field of latex production. Latex is a surfactant stabilized dispersion of polymeric particles in water. Current industrial methods to isolate such polymeric product involve addition of salts to coagulate the dispersion, followed by filtration and washing to remove surfactant and metal salts from the product. When the washing step is ineffective in removing surfactant, the resulting polymers are hydrophilic, which may be undesirable. An alternative method is polymerization in organic solvent. Here, removal of the solvent is time-consuming, costly, and difficult because of the product's high viscosity.

Whether deactivation of the surfactant is desired, or its complete removal, switchable surfactants of the invention present advantages. Their presence would allow the desired polymer particle size to be achieved while allowing the polymer to precipitate from solution when the switchable surfactant is turned "off".

It should also be noted that switchable surfactants of the invention have application in latex paints and other coating formulations since they can turn off when the paint or coating is applied to a surface in air.

A switchable surfactant of the invention can be used in inverse emulsion polymerization of water soluble polymers. In general, water-soluble polymers and/or hygroscopic polymers are prepared by polymerization of an inverse emulsion of a monomer in a hydrophobic solvent. An inverse emulsion has as its continuous phase an organic solvent and has micelle cores present to surround a hydrophilic monomer. With the presence of a switchable surfactant, this inverse emulsion mixture is stabilized and a polymerization reaction is possible. At completion of the polymerization, the surfactant is switched off by application flushing gas to the mixture. The "off" surfactant then partitions into the organic solvent and the polymer precipitates. This permits manufacture of very high molecular weight polymers which are recovered from the inverse emulsion and dried to produce a product (dry-form high MW or branched polymers) that could not be achieved in a standard solution polymerization process because of the tendency for such products to form gels. Low HLB (hydrophile/lipophile balance) switchable surfactants are preferred in this application, and the surfactant should not act as a chain-transfer agent. Polymers that are expected to be readily prepared by this method include, for example, polyacrylamide, polyacrylic acid, polymethacrylic acid, alkali metal salts of polyacrylic acid or polymethacrylic acid, tetraalkylammonium salts of polyacrylic acid or polymethacrylic acid, polyvinylalcohols, and other hygroscopic polymers or polymers that are substantially soluble in water or that swell in water.

In some polymerization applications, the surfactant becomes a part of the polymeric particle product, allowing the particles to be precipitated and resuspended repeatedly.

Switchable surfactants of the invention can find use as transient antifoams in distillation columns, replacing traditional cationic surfactants.

Another application for reversibly switchable surfactants is protection and deprotection of nanoparticles. Nanoparticles and other materials are frequently temporarily protected during synthetic procedures by traditional surfactants. They could be more readily deprotected and cleaned if reversibly switchable surfactants were used. The switchable surfactants and methods of use thereof according to the invention can lessen environmental impact of industrial processes, both by saving energy normally expended during separations and by improving the purity of wastewater emitted from production facilities. The presence of a switchable surfactant in waste effluent could lead to significantly less environmental damage since effluent can be readily decontaminated by treatment with the appropriate trigger prior to its release into the environment.

WORKING EXAMPLES

Materials $CO_2$ (Praxair, SFC grade, 99.998%), argon (Praxair, 99.998%) and air (Praxair, extra-dry grade) were used as received. A sample of commercial light crude oil was donated by Shell. A sample of Federated light crude was donated by Imperial Oil through Environment Canada. A sample of B-heavy crude oil (density 0.89 g/mL) was purchased from Nacalai Tesque, Inc. through Fisher Scientific, Ottawa, Ontario, Canada (Code 44132-04). Alaska North Slope (ANS) heavy crude oil was provided through NOM (U.S. National Oceanographic and Atmospheric Administration). Scotian light gas condensate (an oil which is a by-product of a gas well off of Nova Scotia) was provided by Department of Fisheries and Oceans Canada. For CMC measurements, water was purified with a Millipore Simplicity™ water purification system to generate water exceeding ASTM Type 1 water quality standards. For all other experiments, deionized water was used. Dimethylacetamide dimethyl acetal was received from TCI America (Tokyo Chemical Industry Co., Ltd.) (Portland, Oreg., USA). All other reagents were received from Aldrich (Oakville, Ontario, Canada).

Example 1

Synthesis and characterization of N'-alkyl-N,N-dimethylacetamidine compounds

Example 1A

Synthesis and characterization of N'-hexadecyl-N,N-dimethylacetamidine (1a) and N'-dodecyl-N,N-dimethylacetamidine (1b)

N'-alkyl-N,N-dimethylacetamidines 1a (N'-hexadecyl-N,N-dimethyl-acetamidine and 1b (N'-dodecyl-N,N-dimethylacetamidine) were synthesized by heating an equimolar amount of the appropriate long chain primary amine with dimethylacetamide dimethyl acetal for 10-20 min at 60° C. without solvent (Scoggins, M. W., J. Chromatograph. Sci. (1975) 13: 146-148) (see FIG. 1C). Methanol, a byproduct, was removed by evaporation under high vacuum. The yield of the N'-alkyl-N,N-dimethylacetamidines was quantitative and was determined gravimetrically. The purity was 90% and was determined by $^1$H NMR spectroscopy. The major impurity was N-alkyl-O-methylacetacetimidate (N-hexadecyl-O-methylacetacetimidate 3a, and N-dodecyl-O-methylacetacetimidate, 3b), as identified by $^1$H NMR and gas chromatography/mass spectroscopy. Either the unpurified 1a or the unpurified 1b could be used as a reversibly switchable surfactant without further purification. However, higher purity samples of the amidines 1a and 1b were obtained by converting them to 2a and 2b, respectively, as described in the following Examples and reconverting them to 1a and 1b, respectively, by suspending in tetrahydrofuran and bubbling with argon for 30 min at room temperature, followed by removing the tetrahydrofuran under reduced pressure.

N'-hexadecyl-N,N-dimethylacetamidine (1a): $^1$H NMR (CDCl$_3$): 0.88 (t, $^3J_{HH}$=6.8 Hz, 3H, CH$_2$CH$_3$), 1.28 (m, 26H, C$_{13}$H$_{26}$), 1.49 (quintet, $^3J_{HH}$=7.6, NCH$_2$CH$_2$C$_{14}$H$_{29}$), 1.87 (s, 3H, CCH$_3$), 2.87 (s, 6H, N(CH$_3$)$_2$), 3.17 (t, $^3J_{HH}$=7.6 Hz, 2H, NCH$_2$). $^1$H NMR (DMSO-d$_6$) 0.85 (t, $^3J_{HH}$=6.4 Hz, 3H, CH$_2$CH$_3$), 1.24 (m, 26H, C$_{13}$H$_{26}$), 1.40 (quintet, $^3J_{HH}$=6.8, NCH$_2$CH$_2$C$_{14}$H$_{29}$), 1.79 (s, 3H, CCH$_3$), 2.76 (s, 6H, N(CH$_3$)$_2$), 3.04 (t, $^3J_{HH}$=6.8 Hz, 2H, NCH$_2$). $^1$H NMR (MeOD-d$_4$) 0.92 (t, $^3J_{HH}$=6.6 Hz, 3H, CH$_2$CH$_3$), 1.32 (m, 29H, C$_{13}$H$_{26}$, CCH$_3$), 1.51 (quintet, $^3J_{HH}$=6.0, NCH$_2$CH$_2$C$_{14}$H$_{29}$), 2.98 (s, 6H, N(CH$_3$)$_2$), 3.25 (t, $^3J_{HH}$=6.4 Hz, 2H, NCH$_2$). $^{13}$C NMR (CDCl$_3$): 12.4, 14.1, 22.7, 27.6, 29.4-29.7 (overlapped peaks), 31.5, 31.9, 32.4, 38.0, 50.0, 158.8. IR (neat): 721 (w), 1008 (m), 1187 (w), 1343 (m), 1464 (m), 1629 (s, v(C=N)), 2825 (s), 2923 (s).

N'-dodecyl-N,N-dimethylacetamidine (1b): $^1$H NMR (CDCl$_3$): 0.89 (t, $^3J_{HH}$=8.8 Hz, 3H, CH$_3$C$_{11}$H$_{22}$), 1.29 (m, 18H, CH$_3$C$_9$H$_{18}$CH$_2$CH$_2$N), 1.51 (quintet, $^3J_{HH}$=9.2 Hz, 2H, CH$_3$C$_9$H$_{18}$CH$_2$CH$_2$N), 1.89 (s, 3H, CCH$_3$), 2.88 (s, 6H, N(CH$_3$)$_2$), 3.18 (t, $^3J_{HH}$=10 Hz, 2H, C$_{11}$H$_{22}$CH$_2$N). $^1$H NMR (DMSO-d$_6$) 0.86 (t, $^3J_{HH}$=8.8 Hz, 3H, CH$_2$CH$_3$), 1.24 (m, 18H, C$_9$H$_{18}$), 1.40 (quintet, $^3J_{HH}$=8.8, 2H, CH$_3$C$_9$H$_{18}$CH$_2$CH$_2$N), 1.79 (s, 3H, CCH$_3$), 2.76 (s, 6H, N(CH$_3$)$_2$), 3.04 (t, $^3J_{HH}$=8.8 Hz, 2H, NCH$_2$). $^1$H NMR (MeOD-d$_4$) 0.92 (t, $^3J_{HH}$=8.8 Hz, 3H, CH$_2$CH$_3$), 1.31 (m, 21H, C$_9$H$_8$, CCH$_3$), 1.49 (quintet, $^3J_{HH}$=8.8, 2H, CH$_3$C$_9$H$_{18}$CH$_2$CH$_2$N), 2.94 (s, 6H, N(CH$_3$)$_2$), 3.22 (t, $^3J_{HH}$=9.6 Hz, 2H, NCH$_2$). $^{13}$C NMR (CDCl$_3$): 12.4, 14.1, 22.7, 27.6, 29.4-29.7 (overlapped peaks), 31.9, 32.4, 38.0, 50.2, 158.8. IR (neat): 1010 (m), 1184 (m), 1343 (s), 1466 (m), 1630 (s, v(C=N)).

Example 1B

Synthesis and characterization of N'-octyl-N,N-dimethylacetamidine (1c) and N'-butyl-N,N-dimethylacetamidine (1d)

N'-octyl-N,N-dimethylacetamidine (1c) was synthesized by heating an equimolar amount of n-octylamine with dimethylacetamide dimethyl acetal for 10-20 min at 60° C. without solvent. Methanol, a byproduct, was removed by evaporation under high vacuum. The yield of N'-octyl-N,N-dimethylacetamidine (1c) was quantitative and was determined gravimetrically. The purity was typically 90% and was determined by $^1$H NMR spectroscopy. The major impurity was N-octyl-O-methylacetacetimidate as identified by $^1$H NMR spectroscopy. Unpurified 1c could be used as a reversibly switchable surfactant without further purification.

N'-octyl-N,N-dimethylacetamidine (1c): $^1$H NMR (CDCl$_3$) 0.88 (t, 3H, CH$_2$CH$_3$), 1.29 (m, 10H, C$_5$H$_{10}$CH$_3$), 1.51 (quintet, 2H, NCH$_2$CH$_2$), 1.88 (s, 3H, CCH$_3$), 2.87 (s, 6H, N(CH$_3$)$_2$), 3.18 (t, 2H, NCH$_2$).

N'-butyl-N,N-dimethylacetamidine (1d) was synthesized from n-butylamine and dimethylacetamide dimethyl acetal by the same method as described above for 1a, 1b and 1c. 1d was subsequently used directly for the preparation of 2d, and a sample of 1d was prepared for characterization purposes by applying strong vacuum to a sample of 2d.

N'-butyl-N,N-dimethylacetamidine (1d): $^1$H NMR (CDCl$_3$) 0.91 (t, 3H, CH$_2$CH$_3$), 1.34 (m, 2H, CH$_2$CH$_3$), 1.52 (quintet, 2H, NCH$_2$CH$_2$), 1.98 (s, 3H, CCH$_3$), 3.00 (s, 6H, N(CH$_3$)$_2$), 3.26 (t, 2H, NCH$_2$). $^{13}$C{$^1$H} NMR (CDCl$_3$) 13.1 (CCH$_3$), 13.9 (CH$_2$CH$_2$CH$_3$), 20.4 (CH$_2$CH$_2$CH$_3$), 33.7 (CH$_2$CH$_2$CH$_3$), 38.9 (NCH$_3$), 48.2 (CH$_2$CH$_2$CH$_3$), 160.0 (CCH$_3$) ppm.

Example 2

Synthesis and characterization of N'-alkyl-N,N-dimethylacetamidinium bicarbonates

Example 2A

Synthesis and characterization of N'-hexadecyl-N,N-dimethylacetamidinium bicarbonate (2a) and N'-dodecyl-N,N-dimethylacetamidinium bicarbonate (2b)

Carbon dioxide gas was bubbled through a solution of the appropriate crude N'-alkyl-N,N-dimethylacetamidine in wet acetonitrile solution (see FIG. 1C). In each case, the resulting white precipitate, the bicarbonate salt of the amidine, was obtained after filtration in 98% yield.

N'-hexadecyl-N,N-dimethylacetamidinium bicarbonate (2a): $^1$H NMR (MeOD-d$_4$) 0.92 (t, $^3J_{HH}$=6.6 Hz, 3H, CH$_2$CH$_3$), 1.32 (m, 29H, C$_{13}$H$_{26}$), 1.64 (quintet, $^3J_{HH}$=6.6), 3.14 (s, 3H, NCH$_3$), 3.27 (s, 3H, NCH$_3$), 3.42 (t, $^3J_{HH}$=7.2 Hz, 2H, NCH$_2$). $^{13}$C NMR (MeOD-d$_4$): 13.1, 22.3, 26.2, 29.0-29.4 (multiple peaks), 29.7, 31.7, 44.5, 160.0, 164.7. IR (KBr): 837 (m, v(CO$_2$) out-of-plane for HCO$_3^-$), 1257 (m), 1418 (m), 1644 (s, v(C=N)). MS e/Z (High resolution): M+H$^+$ expected for C$_{20}$H$_{43}$N$_2$ 311.3426, observed 311.3414. MS e/Z (electrospray anionic, low resolution): M expected for HCO$_3^-$ 61.0, observed 60.6. Note that CCH$_3$ protons undergo deuterium exchange with CD$_3$OD and are therefore not visible in the $^1$H NMR spectrum.

N'-dodecyl-N,N-dimethylacetamidinium bicarbonate (2b): $^1$H NMR (MeOD-d4) 0.92 (t, $^3J_{HH}$=6.4 Hz, 3H, CH2CH3), 1.34 (m, 29H, C13H26), 1.64 (quintet, $^3$JHH=6.8), 3.15 (s, 3H, NCH3), 3.28 (s, 3H, NCH3), 3.42 (t, $^3J_{HH}$=7.2 Hz, 2H, NCH2) $^{13}$C NMR (MeOD-d$_4$) 13.0, 22.3, 26.2, 29.0-29.3 (multiple peaks), 29.7, 31.7, 44.5, 160.0, 164.6. IR (KBr): 833 (m, bicarbonate), 1007 (w), 1404 (m), 1651 (s, v(C=N)). MS e/Z (low resolution): M expected for C$_{16}$H$_{35}$N$_2$ 255.5, observed 255.3. MS (ES anionic, low resolution): M expected for HCO$_3$ 61.0, observed 61.2. Note that CCH$_3$ protons undergo deuterium exchange with CD$_3$OD and are therefore not visible in the $^1$H NMR spectrum.

Example 2B

Synthesis and characterization of N'-octyl-N,N-dimethylacetamidinium bicarbonate (2c)

To prepare 2c, carbon dioxide gas was bubbled through a solution of the crude N'-octyl-N,N-dimethylacetamidine in wet diethyl ether for at least 2 h without stirring. The CO$_2$ bubbling was continued to remove most of the diethyl ether by evaporation. A white solid mixed with a yellow oil was obtained. Acetonitrile was added and the resulting suspension was filtered at once through a medium porosity frit. A solid was obtained and was washed with acetonitrile. The resulting clean white solid was characterized as follows.

N'-octyl-N,N-dimethylacetamidinium bicarbonate (2c): $^1$H NMR (CDCl$_3$) 0.80 (t, 3H, CH$_2$CH$_3$), 1.15-1.30 (m, 10H, C$_5$H$_{10}$CH$_3$), 1.38 (quintet), 1.90 (s), 3.14 (s, 3H, NCH$_3$), 3.27 (s, 3H, NCH$_3$), 3.42 (t, $^3J_{HH}$=7.2 Hz, 2H, NCH$_2$). IR (KBr): 633 (m), 722 (m), 760 (m), 818 (m), 837 (w, bicarbonate), 965 (m), 1329 (s), 1464 (m), 1694 (s). MS e/Z (electrospray anionic, low resolution): M expected for $C_{12}H_{27}N_2^+ + HCO_3^- + Na^+$: 283.2, observed 283.0.

Example 2C

Synthesis and characterization of N'-butyl-N,N-dimethylacetamidinium bicarbonate (2d)

N'-butyl-N,N-dimethylacetamidinium bicarbonate (2d) was prepared by mixing crude 1d with wet acetonitrile and bubbling $CO_2$ through the mixture for 2 h. Crystals of 2d precipitated and were collected by gravity filtration through filter paper under air. The solid precipitate that was collected on the filter paper was washed with ether. Importantly, vacuum filtration is not used because vacuum treatment removes the $CO_2$ and converts the solid product into a liquid (presumably 1d). The product, N'-butyl-N,N-dimethylacetamidinium bicarbonate (2d) was obtained as crystals of sufficient quality for determination of the structure by X-ray crystallography.

N'-butyl-N,N-dimethylacetamidinium bicarbonate (2d): $^1$H NMR ($CD_3OD$) 0.9 (t, 3H, $CH_2CH_3$), 1.3 (m, 2H, $CH_2CH_3$), 1.5 (quintet, 2H, $NCH_2CH_2$), 3.0 (s, 3H, $NCH_3$), 3.2 (s, 3H, $NCH_3$), 3.3 (t, 2H, $NCH_2$). Note that $CCH_3$ protons undergo deuterium exchange with $CD_3OD$ and are therefore not visible in the $^1$H NMR spectrum.

Specifically, a crystal of 2d compound (colorless, plate-shaped, size 0.35×0.08×0.03 mm) was mounted on a glass fiber with grease and cooled to −93° C. in a stream of nitrogen gas controlled with Cryostream Controller 700. Data collection was performed on a Bruker SMART APEX II X-ray diffractometer with graphite-monochromated Mo $K_\alpha$ radiation ($\lambda$=0.71073 Å), operating at 50 kV and 30 mA over 2θ ranges of 4.94~50.00°. No significant decay was observed during the data collection. Data was processed on a PC using Bruker AXS Crystal Structure Analysis Package. Data collection: APEX2 (Bruker, 2006 available through Bruker BioSpin Ltd., Milton, Ontario, Canada); cell refinement: SAINT (Bruker, 2005); data reduction: SAINT (Bruker, 2005); structure solution: XPREP (Bruker, 2005) and SHELXTL (Bruker, 2000); structure refinement: SHELXTL; molecular graphics: SHELXTL; publication materials: SHELXTL. Neutral atom scattering factors were taken from Cromer and Waber (Cromer, D. T.; Waber, J. T. *International Tables for X-ray Crystallography*; Kynoch Press: Birmingham, UK, 1974; Vol. 4, Table 2.2 A). The crystal was orthorhombic space group Pna2$_1$, based on the systematic absences, E statistics and successful refinement of the structure. The structure was solved by direct methods. Full-matrix least-square refinements minimizing the function $\Sigma w(F_o^2 - F_c^2)^2$ were applied to the compound. All non-hydrogen atoms were refined anisotropically. The hydrogen atoms on the bicarbonate (H1h), the one on the nitrogen (H1n), and the acetonitrile (H10a, H10b and H10c) were located from difference Fourier maps, and all the other hydrogen atoms were calculated and their contributions were included in the structure factor calculations. Convergence to final $R_1$=0.0633 and $wR_2$=0.1822 for 1734 (I>2σ(I)) independent reflections, and $R_1$=0.0867 and $wR_2$=0.2068 for all 2378 (R(int)=0.0264) independent reflections, with 174 parameters and 0 restraints, was achieved. The largest residual peak and hole were 0.526 and −0.497 e/Å$^3$, respectively.

The contents of the unit cell are shown in FIG. 9. Each unit cell contains two N'-butyl-N,N-dimethylacetamidinium cations, two bicarbonate anions, and two acetonitrile solvent molecules.

Example 2C

Synthesis and characterization of N'-hexyl-N,N-dimethylacetamidine (1e)

N'-hexyl-N,N-dimethylacetamidine (1e) was synthesized by heating n-hexylamine (2.03 mL) with dimethylacetamide dimethyl acetal (2.5 mL) for 20 min at 60° C. under $N_2$ in a 2-neck round bottom flask without solvent. A yellow solution formed and was allowed to cool. Methanol, a byproduct, was removed by evaporation under high vacuum. Diethyl ether (15 mL) and distilled water (3 drops) were added and $CO_2$ was bubbled through the mixture for 1 h to convert the crude 1e into the bicarbonate salt 2e. The mixture was then put in a freezer for 30 min because the white solid so formed degrades back to the liquid readily upon exposure to air. This frozen material was used as the crude surfactant for emulsion stability tests. A sample of 1e was prepared by applying strong vacuum to a portion of the frozen material at room temperature.

N'-hexyl-N,N-dimethylacetamidine (1e): $^1$H NMR ($CDCl_3$) 0.81 (t, 3H, $CH_2CH_3$), 1.23 (m, 6H, $C_3H_6CH_3$), 1.43 (quintet, 2H, $NCH_2CH_2$), 1.81 (s, 3H, $CCH_3$), 2.80 (s, 6H, $N(CH_3)_2$), 3.10 (t, 2H, $NCH_2$). $^{13}C\{1H\}$ NMR ($CDCl_3$) 12.4 ($CCH_3$), 14.1 (hexyl C6), 22.7 (hexyl C5), 27.3 (hexyl C3), 31.9 (hexyl C4), 32.4 (hexyl C2), 37.0 ($NCH_3$), 50.2 (hexyl C1), 158.7 ($CCH_3$) ppm.

Example 3

Reversible Conversion of Amidine Compounds N'-alkyl-N,N-dimethylacetamidine to Surfactants

Example 3A

Reversible conversion of N'-hexadecyl-N,N-dimethylacetamidine (1a) and N'-dodecyl-N,N-dimethylacetamidine (1b) to surfactants To confirm that amidines could be converted to amidinium bicarbonates by exposure to carbon dioxide in the presence of water, the following experiment was performed. Independently, two amidines, 1a (see FIG. 1C) and 1b, were prepared and characterized. Each of 1a and 1b was placed in diethyl ether, the solution was bubbled with $CO_2$, and the resulting precipitate was isolated and characterized as amidinium bicarbonate salt (2a, 2b). Each of the bicarbonate salts was then reconverted into the amidine 1a, 1b by bubbling argon through a solution of 2a, 2b in toluene. The isolated reconverted 1a and 1b were characterized by $^1$H NMR and IR spectroscopy (see Example 1).

Example 3B

Test of ability of N'-octyl-N,N-dimethylacetamidinium bicarbonate (2c), N'-butyl-N,N-dimethylacetamidinium bicarbonate (2d), and N'-hexyl-N,N-dimethylacetamidinium bicarbonate (2e) to stabilize an emulsion 2d (50 mg) was put in a mixture of water (2 mL) and hexadecane (4 mL) in a glass vial. $CO_2$ was bubbled through the mixture for 30 min. The vial was then capped and shaken for 10 min using a Retsch MM2 mixer mill (Retsch, Haan, Germany). An emulsion did not form even after 10 min of sonication and 10 min of shaking. Two clear and separate liquid phases were observed both before and immediately after the shaking. The same experiment but without the $CO_2$ treatment gave the same result. Thus, 2d did not stabilize the emulsion, as was expected given that the invention involves a compound having a long chain ($C_5$ or more) or other hydrophobic moiety.

2c (50 mg) was put in a mixture of water (2 mL) and hexadecane (4 mL) in a glass vial. $CO_2$ was bubbled through the mixture for 30 min. The vial was then capped and shaken for 10 min using a Retsch MM2 mixer mill. A stable emulsion formed with some clear liquid present. This is supportive of the especially preferred chain length of 8 or more hydrocarbon units for at least one R group of the amidine compound.

2e (100 mg) was put in a mixture of water (2 mL) and hexadecane (4 mL) in a glass vial. $CO_2$ was bubbled through the mixture for 30 min. The vial was then capped and sonicated for 10 min followed by shaking for 10 min using a Retsch MM2 mixer mill. The final result was an unstable emulsion, that persisted only for several minutes.

Example 4

Thermogravimetric analysis of
N'-hexadecyl-N,N-dimethylacetamidinium
bicarbonate (2a)

In an initial study, thermogravimetric analysis (TGA) was used to determine the optimum temperature for driving off carbon dioxide from a solid sample of N'-hexadecyl-N,N-dimethylacetamidinium bicarbonate (2a). A solid sample of 2a heated to 300° C. at a rate of 20° C./min showed TGA peaks at 62° C. (3% loss), 76° C. (further 12% loss) and 226° C. (almost complete loss). The first two peaks, which were partly merged, were consistent with water and $CO_2$ loss (expected 5% and 12% loss) respectively.

In a subsequent TGA study, a sample of N'-hexadecyl-N, N-dimethylacetamidinium bicarbonate (2a) (1.492 mg) was heated to 350° C. at a rate of 5° C./min in a TGA Q500 (TA Instruments, New Castle, Del., USA). The mass loss of 15.5% from 50° C. to 63° C. corresponds to the mass of $CO_2$ and water (theoretical mass 16.6% of 2a) (Liu, Yingxin; Jessop, Philip G.; Cunningham, M.; Eckert, Charles A.; Liotta, Charles L. "Switchable Surfactants," *Science* (2006) 313: 958-960 with supporting material www.sciencemag.org/cgi/content/full/313/5789/958/DC).

Example 5

Conductivity measurement of amidine compound
N'-hexadecyl-N,N-dimethylacetamidinium
bicarbonate (2a)

The reversibility and repeatability of the conversion of 1a to 2a were confirmed by monitoring the conductivity using a JENWAY conductivity meter 4071 of a solution of 1a, 2a in dimethylsulfoxide (DMSO) while carbon dioxide and then argon were bubbled through the solution for 3 cycles (see FIG. 2).

In a separate but similar experiment, air was found to have the same effect as argon. When air was bubbled through a solution of 1a in wet DMSO, the conductivity did not show an obvious rise, whereas when $CO_2$ was bubbled through, conductivity rose significantly. That is, the conductivity increase indicated the presence of the product of the reaction of amidine with $CO_2$ and water. As air was bubbled through the resulting solution of 2a in DMSO, the conductivity dropped down gradually. Because the reaction is reversible, the reaction equilibrium is affected by the partial pressure of $CO_2$, and the $CO_2$ concentration in air is too low (0.038% by volume or pressure), therefore the partial pressure of $CO_2$ in air is insufficient to switch 1a to 2a, but air can drive $CO_2$ out of the solution.

In a blank experiment, conductivity did not change when $CO_2$ was bubbled through wet DMSO in the absence of amidine. Therefore carbonic acid has little conductivity in the wet DMSO.

Example 6

Solubilization of Nile Red by
N'-hexadecyl-N,N-dimethylacetamidinium
bicarbonate (2a)

The following experiment was performed to study the use of a reversible switchable surfactant at atmospheric pressure to solubilize a hydrophobic dye, Nile Red. This experiment showed that compound 2a was capable of acting as a surfactant and facilitated the dissolution in an aqueous solution of 2a of a dye that is not otherwise soluble in water. Following the solubilization, compound 2a was converted to compound 1a and the dye was observed to be insoluble in the aqueous solution of 1a.

Distilled water (3.5 mL) was added to a glass vial at atmospheric pressure in open air. Nile Red (in excess) was added to the vial in solid form. The dark coloured Nile Red dye did not dissolve but remained in suspension in the clear colourless water. The vial containing the suspension was capped and sonicated for 3 minutes, after which the contents appeared as a faint pink transparent suspension with dark flakes on the bottom and surface of the water. Compound 2a (20 mg) was added and the vial containing the suspension was capped and shaken by hand for 30 seconds. The contents then appeared as a dark purple transparent solution with a small amount of undissolved Nile Red on the bottom and surface of the solution. The solution was allowed to stand overnight. The following morning, the dark purple solution remained unchanged in appearance. The solubilization of the Nile Red in this aqueous solution demonstrated the surfactant properties of compound 2a.

The vial of purple solution was suspended in a water bath which was maintained at 75° C. and a stream of argon gas was bubbled through the hot solution for 3 hours. At the end of the 3 hours, the vial contents appeared as a clear colourless solution with dark coloured material floating on the top and lying on the bottom of the vial. Thus, compound 2a was converted to compound 1a under the influence of the heat and the argon stream. Since compound 1a is a non-surfactant, the Nile Red precipitated out of solution and the solution no longer appeared coloured.

Example 7

Emulsion Studies

Example 7A

Shake Testing of the Ability of Amidinium
Bicarbonate 2a to Stabilize a Higher Alkane/Water
Emulsion The ability of new compound 2a to stabilize a higher alkane/water emulsion was evaluated. Hexadecane (4 mL), water (2 mL), and 1a (90 mg) were combined in a septum-capped vial under argon. The flask was then shaken in a Retsch MM2 mixer mill at a speed setting of 100 for 10 min.

A stable emulsion was not obtained under argon. Although an emulsion formed, it was unstable and separated into two somewhat cloudy layers within 5 minutes after the cessation of shaking.

However, when the mixture was treated with $CO_2$ (i.e., 1a was converted to 2a) before the shaking, the emulsion was much more stable. $CO_2$ gas was bubbled through the solution for 1 h. The flask was then shaken in a Retsch MM2 mixer mill at a speed setting of 100 for 10 min. The vial was then placed on a bench and photographed at various time intervals. It showed no evidence of separation for 3 h, at which point a thin layer of cloudy (but not frothy) liquid began to appear at the bottom of the flask. After 24 h, the thin cloudy layer had grown to 18% of the volume of the sample, while the emulsion still occupied 82% of the volume. After the photograph at 24 h, the sample was flushed with argon at 65° C. for 2 h, thus converting 2a to 1a. This resulted in an entirely clear separation of the hexadecane and water layers; both layers were transparent, not cloudy. Similar tests were performed with 1a using decane, and with 1a and hexane in place of the hexadecane, with similar results.

Experiments with a traditional non-switchable surfactant (dioctyl sulfosuccinate, sodium salt) generated a stable emulsion after shaking with 4 mL decane and 2 mL water. However, argon bubbling with heat did not separate the emulsion. This confirmed that argon treatment with heat does not break emulsions stabilized by non-switchable surfactants, and therefore that the 2a-stabilized emulsion separated upon such treatment because argon bubbling and heating removed $CO_2$ from the amidinium bicarbonate salt and switched off the surfactant.

Emulsions prepared by a combination of shaking and sonication were more stable than those prepared by shaking alone. 4 mL hexadecane, 2 mL water, and 90 mg 1a were combined in a septum-capped vial under $CO_2$. $CO_2$ gas was bubbled through the mixture for 1 h (converting 1a to 2a). The vial was then sonicated in a Fisher FS 30 sonicator for 10 min and subsequently shaken in a Retsch MM2 mixer mill at a speed setting of 100 for 10 min. The resulting emulsion did not separate within two weeks. When heated to 65° C. and flushed with argon (to form "off" surfactant) for 2 hours, the liquid mixture separated into two phases: a clear upper phase and a lower emulsion phase. A sample given the same shaking and sonication treatment under argon (with 1a "off" surfactant) separated into two phases within 1 hour, an upper clear liquid and a lower cloudy liquid.

Emulsions stabilized by 2a are best prepared by adding 2a to higher alkane and then adding water, stirring for 30 min, and then applying shear or shaking to generate an emulsion.

Example 7B

Effect of pH on Emulsion Stability

Decane (4 mL), a selected buffer solution (2 mL), and 1a (90 mg) were combined in a septum-capped vial and shaken in a Retsch MM2 mixer mill at a speed setting of 100 for 10 min. Stability of the resulting emulsions is presented in Table 1.

TABLE 1

Stability of emulsions in buffer solution[a] at different pH

| pH | Buffer Solution | Result |
| --- | --- | --- |
| 3 | 1 M NaAc (0.05 mL) and 1 M HAc (3 mL) | Good emulsion |
| 4 | 1 M NaAc (3.9 mL) and 1 M HAc (5 mL) | Good emulsion |
| 5 | 1 M NaAc (6.9 mL) and 1 M HAc (1 mL) | Good emulsion |

TABLE 1-continued

Stability of emulsions in buffer solution[a] at different pH

| pH | Buffer Solution | Result |
| --- | --- | --- |
| 6 | 1 M $NaH_2PO_4$ (5 mL) and 0.25 M $Na_2B_4O_7$ (3 mL) | Part emulsion[b] |
| 7 | 1 M $NaH_2PO_4$ (5 mL) and 0.25 M $Na_2B_4O_7$ (8.5 mL) | Good emulsion |
| 8 | 0.25 M $Na_2B_4O_7$ (6.8 mL) and 1 M HCl (1.2 mL) | Good emulsion |
| 10 | 1 M $Na_2CO_3$ (3 mL) and 1 M $KHCO_3$ (2 mL) | Two clear phases |

[a]4 mL hexadecane/2 mL buffer solution/90 mg 1a, after shaking for 10 min
[b]Three phases were present. The upper layer was oil, the middle layer was emulsion, and the lower layer was aqueous phase, all of roughly equal volume.

Example 7C

Shake Testing of the Ability of Amidinium Bicarbonate 2a to Stabilize a Crude Oil/Water Emulsion Similar experiments to Example 7A were performed with crude oil. Crude oil (4 mL), when shaken for 10 minutes with water (2 mL) but without any additive, was able to form a fairly stable emulsion. The same mixture of oil and water but additionally with surfactant compound 2a also formed a fairly stable emulsion. However, the oil and water mixture under argon with non-surfactant 1a added formed an unstable emulsion which separated into two layers within 30 minutes. This result indicates that 1a acts as a demulsifier. The detailed procedure, including controls, follows.

i) Crude oil (Shell, 4 mL), water (2 mL), and 1a (90 mg) were combined in a septum-capped vial under $CO_2$. $CO_2$ gas was bubbled through the solution for 1 h, converting 1a to 2a. The flask was then shaken in a Retsch MM2 mixer mill at a speed setting of 100 for 10 min. The vial was then placed on a bench and photographed after various time intervals. The mixture formed a stable emulsion that showed no sedimentation for 2 h.

ii) Crude oil (Shell, 4 mL), water (2 mL), and 1a (90 mg) were combined in a septum-capped vial under Ar. Ar gas was bubbled through the solution for 1 h. The flask was then shaken in a Retsch MM2 mixer mill at a speed setting of 100 for 10 min. The vial was then placed on a bench and photographed after various time intervals. After 30 min, the emulsion had separated.

iii) Crude oil (Shell, 4 mL) and water (2 mL) with no amidine were combined in a septum-capped vial under Ar. Ar gas was bubbled through the solution for 1 h. The flask was then shaken in a Retsch MM2 mixer mill at a speed setting of 100 for 10 min. The vial was then placed on a bench and photographed after various time intervals. The mixture formed a stable emulsion which showed no sedimentation for 6 h.

Results of four different crude oils in shake tests with (i) C16 amidine in its "on" form (compound 2a); (ii) C16 amidine in its "off" form (compound 1a); and (iii) no C16 amidine, are presented in Table 2. (When persistent emulsions were observed, the observation time listed in the table is the total amount of observation time for that sample, and does not imply a difference between samples). Light crude oils from Imperial Oil (Federated crude, 2% asphaltenes) and Shell (density 0.84 g/mL) gave substantially identical results. (Asphaltene assists formation of or stabilizes an emulsion.) Scotian light gas condensate (very light) tested contained extremely low asphaltene. Similar experiments with heavy crude oil high in asphaltene, specifically, B-Heavy (0.89 g/mL) and Alaskan North Slope (ANS), gave much more stable emulsions. The former (not depicted in the table) showed no separation after 1 day in experiments with no amidine or with amidine under $CO_2$, and only partial separation after 16 h for the experiment with non-surfactant/demulsifier 1a under argon.

TABLE 2

Results of shake tests with crude oils, water and C16 amidine.

| Crude Oil | Amidine | $CO_2$ treatment | Wait time | Result |
|---|---|---|---|---|
| Scotian | Off | No | None | emulsion separated in 2 min |
| Scotian | None | No | None | no emulsion |
| Scotian | Off | Yes | None | emulsion separated immediately |
| Scotian | On | No | 30 min | emulsion separated immediately |
| Federated | Off | No | None | emulsion separated after 5 min |
| Federated | None | No | None | no separation in 1 h |
| Federated | Off | Yes | None | emulsion starts separating after 40 min |
| Federated | On | No | 30 min | emulsion starts separating after 40 min |
| ANS | Off | No | None | emulsion, with no separation within 1.5 h |
| ANS | None | No | None | emulsion, with no separation within 1.5 h |
| Shell | Off | No | None | emulsion separated in 30 min |
| Shell | No | No | None | emulsion, with no separation within 4 h |
| Shell | Off | Yes | None | emulsion, with no separation within 4 h |

4 mL crude oil, 2 mL distilled water, 10 min shaking. C16 amidine added in "on" form (106 mg) or "off" form (90 mg) or not at all. $CO_2$ treatment, if used, was 1 h and preceded shaking. Wait time, if used, was 30 min and preceded shaking.

Example 7D

Minimizing Emulsion Droplet Size

Studies have been conducted to determine factors that influence droplet size, emulsion stability, and ease of breaking the emulsion by turning "off" the switchable surfactant. Styrene/water and hexadecane/water mixtures were selected for these tests, and the following conditions were varied: amount of switchable surfactant; emulsion generation method (e.g., shaking, sonication).

A combination of shaking and sonicating was found to be more effective in forming a stable emulsion than either alone. Sonicating alone is more effective than shaking alone. Specifically, surfactant 2b was placed in a 6 dram glass vial. Hexadecane or styrene (0.5 mL) was added, followed by water (4.5 mL). The vial was capped with a rubber septum. A thin steel tube was inserted through the septum into the liquid phase. $CO_2$ was bubbled through the liquid via this tube for 30 min. The septum was then replaced with a plastic cap. A solid silicone sheet was wrapped around the seam between the cap and vial. The sample was then either merely sonicated, merely shaken for 10 min using the Retsch MM2 mixer mill, or both sonicated and shaken for 10 min using the Retsch MM2 mixer mill. The droplet sizes of resulting emulsions were measured using a Mastersizer Hydro 2000S using the method below, results are as indicated in Tables 3 and 4.

Emulsion droplet size was measured by bubbling $CO_2$ for 20 min through a room-temperature distilled water sample contained in a sample chamber of the Mastersizer. One minute after the cessation of bubbling, a background measurement was taken. Then increasing amounts of the emulsion sample were added until the Mastersizer equipment indicated sufficient signal, at which time droplet size measurement was initiated.

TABLE 3

Droplet size in emulsions of hexadecane and water stabilized by 2b.

| Mass of 2b, mg | Sonication time, min | Shaking time, min | Droplet size, µm | Ability to separate[a] |
|---|---|---|---|---|
| 100 | 10 | 0 | 62 | No |
| 100 | 0 | 10 | 164 | No |
| 50 | 10 | 0 | 79 | No |
| 50 | 5 | 0 | 92 | No |
| 50 | 1 | 0 | 145 | Yes |
| 50 | 0 | 10 | 160 | No |
| 25 | 5 | 0 | 15 | No |
| 25 | 4 | 10 | 6.9 | Yes |
| 25 | 4 | 0 | 7.9 | Yes |
| 25 | 1 | 0 | 71 | Yes |
| 20 | 6 | 10 | 0.87 | Yes |
| 20 | 6 | 0 | 5.3 | Yes |
| 20 | 5 | 10 | 3.5 | Yes |
| 20 | 5 | 10 | 6.7 | Yes |
| 20 | 5 | 0 | 2.9 | Yes |
| 20 | 5 | 0 | 2.5 | Yes |
| 20 | 4 | 10 | 3.5 | Yes |
| 20 | 4 | 10 | 2.4 | Yes |
| 20 | 4 | 0 | 4.2 | Yes |
| 20 | 4 | 0 | 5.2 | Yes |
| 20 | 2.5 | 0 | 3.5 | Yes |
| 20 | 1.5 | 0 | 5.1 | Yes |
| 15 | 2 | 0 | 3.5 | Yes |
| 15 | 1 | 0 | unstable[b] | — |

[a]Ability to separate, after 2 h of bubbling argon through the mixture at 65° C., into two layers having volumes approximately equal to the volumes of water and hexadecane originally added. The lower layer was cloudy.
[b]No stable emulsion was obtained.

TABLE 4

Droplet size in emulsions of styrene and water stabilized by 2b.

| Mass of 2b, mg | Sonication time, min | Shaking time, min | Droplet size, µm | Ability to separate[a] |
|---|---|---|---|---|
| 80 | 4 | 0 | 181 | Yes |
| 50 | 4 | 0 | 83 | Yes |
| 20 | 4 | 0 | 30 | Yes |
| 20 | 2.5 | 0 | 57 | Yes |
| 20 | 1.5 | 0 | 46 | Yes |
| 15 | 2 | 0 | 87 | Yes |
| 15 | 1 | 0 | 47 | Yes |

[a]Ability to separate, after 2 h of argon bubbling through the mixture at 65° C., into two layers having volumes approximately equal to the volumes of water and styrene originally added. The lower layer was cloudy.

Example 8

Critical Micelle Concentration Determination of Amidinium Bicarbonate 2a

Figure 3:
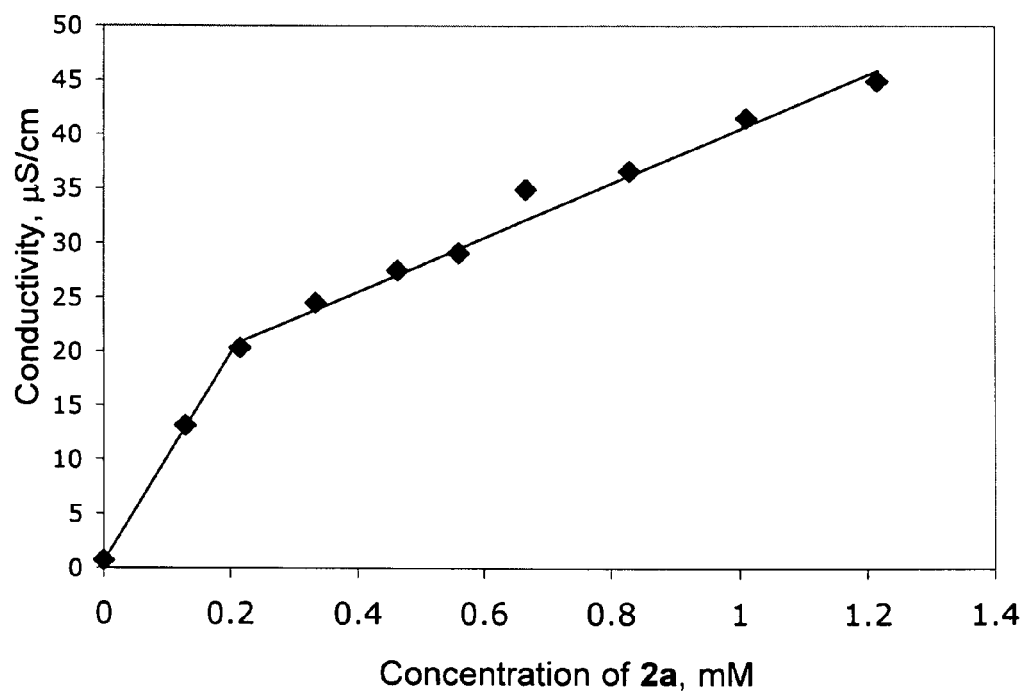
FIG. 3 shows a plot of conductivity of aqueous solutions of 2a as a function of concentration, wherein the break in the line indicates the approximate critical micelle concentration (CMC).

In an initial study, the conductivity of various concentrations of 2a in purified (see above) water was measured using a JENWAY conductivity meter 4071 (Jenway, Barloworld Scientific Ltd, Essex, England), as shown in FIG. 3 and described in Example 5. The CMC for 2a was determined from a plot (see FIG. 3) of the conductivity of the compound (obtained by the conductivity meter studies of Example 5) in water as a function of concentration of compound 2a. The approximate CMC was 0.2 mM, the concentration at the breakpoint of the plot of conductivity versus concentration.

Figure 5:
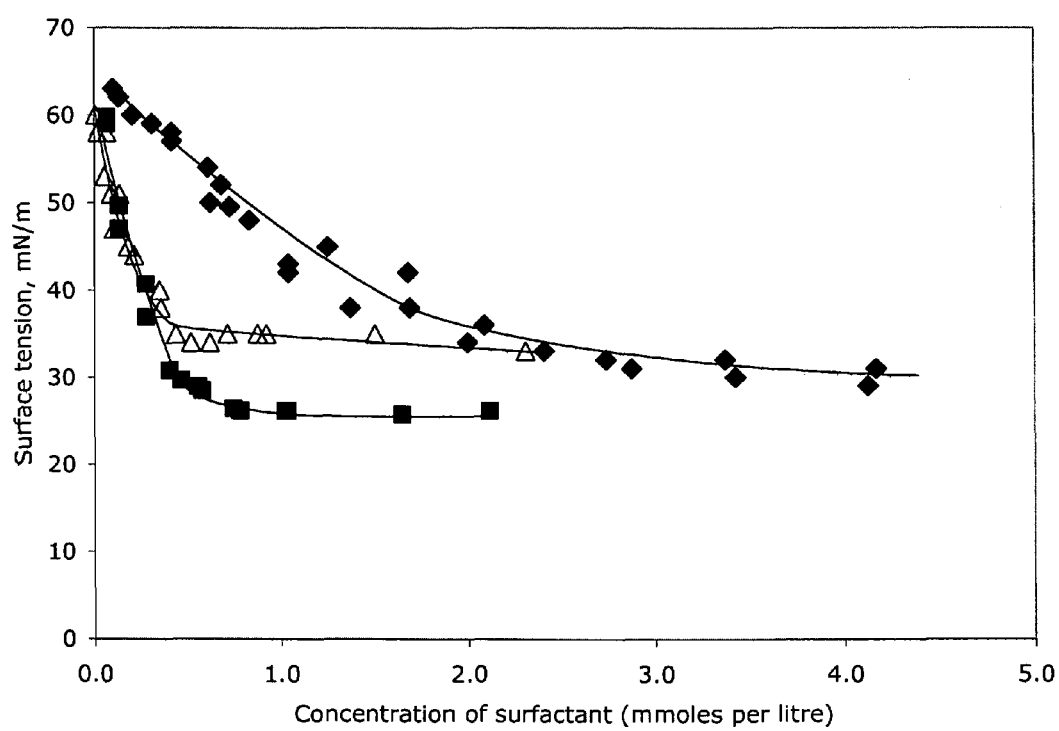
FIG. 5 shows a plot of surface tension as a function of concentration of surfactant in aqueous solution at room temperature as measured by the De Nouy ring technique. 1a•HCl (Δ); 1b•HCl (◆); and 2b (■).
Figure 6:
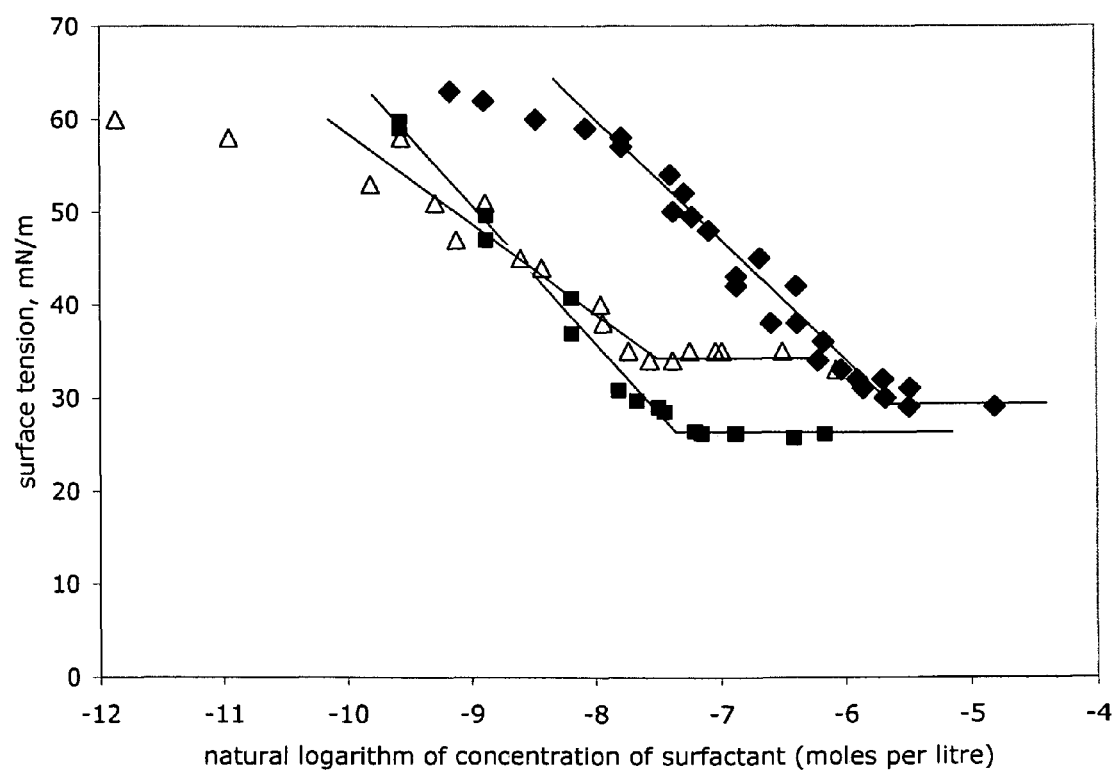
FIG. 6 shows a plot of surface tension as a function of logarithm of concentration of surfactant in aqueous solution at room temperature. 1a•HCl (Δ), 1b•HCl (♦), and 2b (■).

In further studies, surface tension of aqueous solutions of surfactant was measured by a De Nouy ring technique (Mulqueen, M.; Huibers, Paul D. T. "Measuring equilibrium surface tensions" *Handbook of Applied Surface and Colloid Chemistry* (2002), 2: 217-224, Holmberg, K (Ed.) John Wiley & Sons Ltd., Chichester, UK) with a Fisher Surface Tensiomat Model 21 (Fisher Scientific, Ottawa, Ontario, Canada) at 21° C. CMC and surface tension at the CMC were determined from break point of the surface tension and logarithm of the concentration curve. See FIGS. 5 and 6 and Table 5; all surface tension values shown are averages of two measurements.

Specifically, solutions of 2b were made from $CO_2$-saturated water, and $CO_2$ was bubbled through each solution again for 2 min immediately before measuring. Measurements were performed with a tensiometer inside a large $CO_2$-filled glove bag that had been flushed with $CO_2$ for 30 min. For these measurements, HCl salts of 1a and 1b were prepared from neat neutral amidine by treatment with an equivalent of 4 M HCl in dioxane, followed by filtration under air to collect dry white product. Surface tension measurements of HCl salts of 1a and 1b were performed under air.

TABLE 5

CMC values for 2b and the HCl salts of 1a and 1b in water at 21° C.

| | CMC, mM | $\gamma_{CMC}$[f] mN/m | $\Gamma$ (mol/cm$^2$)[d] | a (nm$^2$)[e] |
|---|---|---|---|---|
| 1a•HCl | 0.5 | 35 | 2.5 × 10$^{-10}$ | 0.65 |
| 1b•HCl | 2.2 | 29 | 2.6 × 10$^{-10}$ | 0.64 |
| 2b | 0.5 | 26 | 3.1 × 10$^{-10}$ | 0.54 |
| [C$_{14}$H$_{29}$NMe$_3$]Br[b] | 3.6[c] | 31 | 2.7 × 10$^{-10}$ | 0.61 |
| [C$_{10}$H$_{21}$Pyr]Br[c] | 4 | 32 | 2.0 × 10$^{-10}$ | 0.83 |
| [C$_{12}$H$_{25}$Pyr]Br[c] | 11 | 33 | 3.3 × 10$^{-10}$ | 0.50 |
| [C$_{14}$H$_{29}$Pyr]Br[c] | 2.7 | 31 | 2.8 × 10$^{-10}$ | 0.60 |

[b]At 30° C. (M. J. Rosen, Surfactants and Interfacial Phenomena, 3rd. ed., John Wiley & Sons, Hoboken, 2004).
[c]At 25° C. (M. J. Rosen, Surfactants and Interfacial Phenomena, 3rd. ed., John Wiley & Sons, Hoboken, 2004).
[d]$\Gamma$ is surface excess concentration
[e]a is area per surfactant molecule at the air/water surface
[f]$\gamma_{CMC}$ is surface tension at the CMC Example 9

Switchable Surfactants and Polymerization Reactions

Example 9A

Emulsion Polymerization of Styrene in the Presence of Amidinium Bicarbonate 2b

Emulsion polymerization using 2b as a surfactant was successfully achieved, as depicted in FIGS. 10-13. Two studies are described here, an initial study and a subsequent study.

In the initial study, thermally-initiated polymerization was performed in a styrene-in-water emulsion stabilized by 2b under $CO_2$ for 5 h at 65-70° C. per the equation below. Specifically, $CO_2$ was bubbled through a stirred mixture of styrene (2 mL), water (8 mL) and 2b (400 mg) for 30 min at room temperature. 2',2'-azobis(2-methylpropinamidine) dihydrochloride (187 mg) was added. The mixture was heated to maintain a temperature between 65-70° C. and the bubbling of $CO_2$ was continued. After 5 h, several drops of hydroquinone solution (2% in water) were added to stop the reaction. A portion of the suspension was removed for particle size analysis using a Malvern Mastersizer 2000 equipped with a Hydro2000S optical unit, which uses laser diffraction to measure particles in the range of 0.01-2000 μm (available through Spectra Research Corporation, Mississauga, Ontario, Canada). The particle size distribution was measured; the number-weighted mean diameter was 2.79 μm, the surface-weighted mean diameter was 7.90 μm, and the weight-weighted mean diameter was 17.0 μm. Switching compound 2b to 2a was effected by bubbling argon through the system for 1 h at 65° C., followed by cooling to room temperature, and allowing the latex (suitable for collection as the desired end product) to settle. The latex particles were identified as polystyrene by $^1$H NMR spectroscopy (W. P. Slichter, J. Chem. Ed. (1968) 45(1): 10-16). Without the argon treatment at 65° C., the latex did not settle within an observation time period of 3 days.

In the further studies, both a 2 h treatment with argon and a single 30-minute $N_2$ treatment were shown to be effective in turning off surfactant and allowing settling of particles. Settling was accelerated by centrifugation (Jouan Centrifuge KR25) for 30 min at 40,000 G. Centrifugation prior to treatment with flushing gas was ineffective. Molecular weight of polymer was determined on a Waters Associates model GPC-2690 liquid chromatograph equipped with a Waters 2410 RI detector (Waters Limited, Mississauga, Ontario, Canada). Separation columns were a series of Styragel HR 5, HR 4E and HMW 7. GPC analyses were performed using filtered toluene (99.99% pure) as eluent at a flow rate of 1.0 mL/min. The instrument was calibrated with commercially available polystyrene standards with molecular weights ranging from 770 to 6,500,000 g/mol. Polymer samples were prepared by dissolving 5-7 mg of polymer in 10 mL of filtered HPLC grade toluene. A 200 μL aliquot of the polymer was injected into the continuous flow of solvent (room temperature toluene) and eluted through three Styragel separation columns. Mn was 276,000, Mw 590,000 and PDI 2.14.

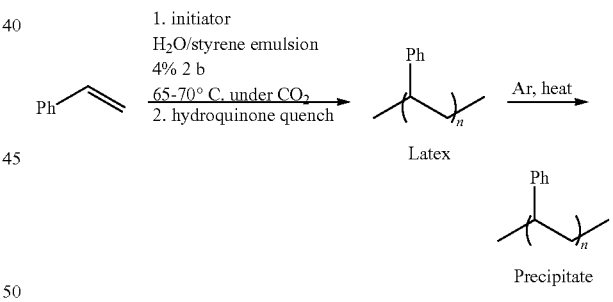

Subsequent studies demonstrated a method for emulsion polymerization of styrene in the presence of 2b in which smaller particles of polystyrene (approximately 0.1 μm or less in diameter) were obtained, as described in detail below. Conveniently, polystyrene particle size can be measured in suspension before the surfactant is turned off.

The surfactant 2b (100 mg) and a teflon-coated magnetic stir bar were placed in a 100 mL three neck flask. A condenser was attached to a first neck, with a rubber septum attached to the top of the condenser. A glass plug was attached to a second neck and a septum was placed on the third neck of the flask. Styrene (0.5 mL) and water (2 mL) were injected through the septum into the flask. Stirring was initiated and $CO_2$ was bubbled through the mixture. A syringe needle was pushed through the septum on the condenser, which allowed $CO_2$ to flow out of the system via an oil bubbler that prevented air from entering the system. CO$_2$ flow was continued for 30 minutes. The CO$_2$ flow was then stopped, the syringes were removed from the septa, and the glass assembly was placed in a sonication bath and sonicated for 4 minutes at room temperature. The syringes were put back into the septa and the CO$_2$ flow was re-initiated. The glass plug was removed, initiator (37 mg of 2',2'-azobis(2-methylpropinamidine)dihydrochloride) was added, and a thermometer with a seal was put in the neck of the flask as a replacement for the glass plug. The flask was heated to 60-65° C. for 5 h. After this reaction time, the flask was cooled back to room temperature and 3 to 4 drops of hydroquinone solution (2% in water) were added. The mixture was stirred for 15 min under argon. A sample of the suspension was withdrawn for particle size analysis. Water (15 mL) was subsequently added to the remaining suspension. The sample was heated to 60° C. for 2 h while argon was bubbled through the solution via the syringes. The sample was then cooled to room temperature and stirred overnight (without argon bubbling). The following morning, the sample was filtered through a medium-porosity glass frit filter. The solid collected on the frit was washed with methanol. A $^1$H NMR spectrum of the collected solid confirmed that the product was polystyrene. A particle size distribution measurement of the product gave the following results: the number-weighted mean diameter was 0.062 μm, the surface-weighted mean diameter was 0.095 μm, and the weight-weighted mean diameter was 0.103 μm.

A similar experiment, but without the hydroquinone solution addition and without the 15 min of stirring under argon, gave similar results. The particle size distribution measurement of the initial product gave the following results: the number-weighted mean diameter was 0.075 μm, the surface-weighted mean diameter was 0.101 μm, and the weight-weighted mean diameter was 0.118 μm.

Example 9B

Microsuspension Polymerization of Methyl Methacrylate in the Presence of 2b/1b

Radical polymerization of methyl methacrylate stabilized by 2b was tested with an azo-based free radical initiator in a methyl methacrylate-in-water emulsion with hexadecane under CO$_2$ (see reaction scheme below). CO$_2$ was bubbled through a reaction mixture of methyl methacrylate (2 mL), water (7.5 mL), hexadecane (0.5 mL) and 2b (400 mg) in a round bottom flask for 30 min at room temperature. Initiator 2',2'-azobis(2-methylpropinamidine)dihydrochloride (187 mg) was added. The mixture was heated to and maintained at 65° C. while bubbling of CO$_2$ continued. The reaction mixture looked like a white emulsion during the polymerization process. After 5 h, several drops of hydroquinone solution (1% in water) were added to quench the reaction.

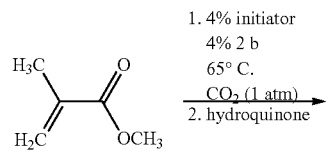

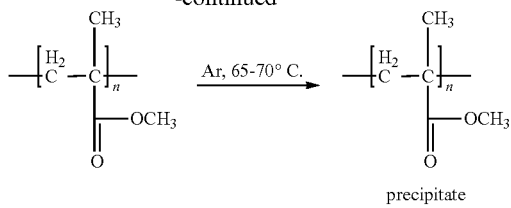

precipitate

A 2 mL sample was taken from the suspension for particle-size analysis using a Mastersizer 2000. Size Exclusion Chromatography (SEC) was performed using Waters μ-styragel HT-4 and 500 Å columns with tetrahydrofuran (THF) as eluent at a flow rate of 1 mL/min. Calibration was based on commercially available polystyrene standards. N$_2$ was bubbled through the remainder of the suspension for 2 h while the temperature was maintained at 65° C. Thus 2b was converted to non-surfactant 1b. Distilled water (10 mL) was subsequently added and the mixture was cooled to room temperature. Solid polymer was collected by filtration. The white solid was dried in an oven at 80° C. for 30 min, dissolved in 5 mL of toluene and 50 mL cold methanol was added to the toluene solution. The polymethylmethacrylate (PMMA) precipitate was filtered and dried in an oven for 30 min. Conversion was 61%.

Figure 7:
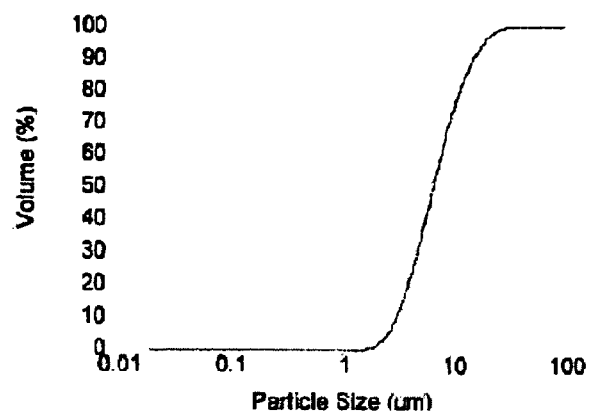
FIG. 7 shows a plot of particle size distribution of polymethylmethacrylate (PMMA) made in the presence of 2b without sonication.
Figure 8:
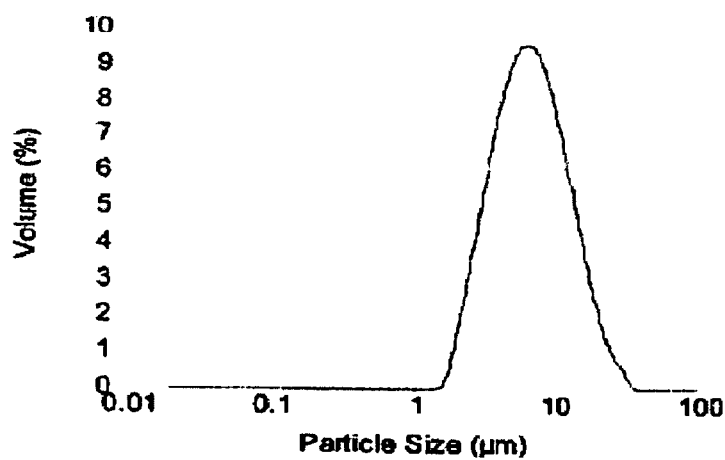
FIG. 8 shows a plot of cumulative particle size distribution of PMMA made in the presence of 2b without sonication.

Characterization of the resulting PMMA was as follows: Mn of 60,300 g/mol, Mw of 88,300 g/mol, and PDI of 1.46. (In comparison, characteristics of certain commercially available PMMA are: Mn of 46,000 g/mol, Mw of 93,000 g/mol, and PDI of 2.02 (Aldrich Chemical Company Catalogue, 2006, Sigma-Aldrich, Canada, Ltd., Oakville, Ontario, Canada).) The number-weighted mean diameter of the collected PMMA particles was 3.36 μm, the surface-weighted mean diameter was 5.60 μm, and the weight-weighted mean diameter was 7.89 μm. The particle size distribution and cumulative particle size distribution are shown in FIGS. 7 and 8.

In the absence of treatment with a flushing gas and conversion of 2b to 1b, the PMMA polymer, stabilized by surfactant 2b, failed to settle within an observation period of 3 days.

Example 10

Studies of Effects of Sodium, Calcium and Iron Salts on Conversion of Amidine Surfactants Experiments to determine if 1a reacts with NaCl, CaCO$_3$ or FeCl$_3$, respectively, were performed. A first mixture was decane (4 mL), water (2 mL), 1a (90 mg) and NaCl (20 mg). A second mixture was decane (4 mL), water (2 mL), 1a (120 mg) and CaCO$_3$ (43 mg). The mixtures were shaken in a Retsch MM2 mixer mill at a speed setting of 100 for 10 min. The resulting mixtures separated into two phases immediately after shaking. That is, NaCl and CaCO$_3$ did not switch on 1a. A third mixture was decane (4 mL), water (2 mL), 1a (120 mg) and FeCl$_3$ (94 mg). This mixture was shaken in the same manner and formed a stable emulsion. This result indicated that FeCl$_3$ can switch on amidine 1a and the resultant compound can stabilize an emulsion.

All publications listed and cited herein are incorporated herein by reference in their entirety. It will be understood by those skilled in the art that this description is made with reference to certain preferred embodiments and that it is possible to make other embodiments employing the principles of the invention which fall within its spirit and scope as defined by the claims.

I claim:

1. A composition comprising:
   (a) water or an aqueous solution;
   (b) a switchable surfactant compound that comprises a hydrophobic portion and a nitrogen-containing salt portion that reversibly converts to a non-salt form upon contact with a source of heat and/or a flushing gas, wherein said flushing gas contains substantially no gas that liberates hydrogen ions in the presence of water;
   (c) a water immiscible liquid that is in a stable emulsion with said water or aqueous solution and forms an unstable emulsion or other two-phase mixture with said water or aqueous solution when the switchable surfactant compound is converted to the non-salt form, or a water insoluble solid that is in a stable suspension with said water or aqueous solution and forms an unstable suspension or other two-phase mixture with said water or aqueous solution when the switchable surfactant compound is converted to the non-salt form; and
   (d) a dissolved gas that liberates hydrogen ions in the presence of water,
   wherein the gas does not include HCN or HCl, and
   wherein the nitrogen-containing portion comprises a protonated amidine moiety or a protonated guanidine moiety.

2. The composition of claim 1, wherein the nitrogen-containing portion comprises a protonated amidine moiety.

3. The composition of claim 2, wherein the switchable surfactant compound comprises the general formula (4)

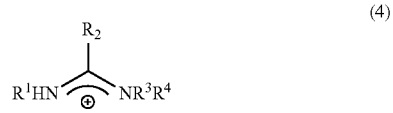

(4)

where
   at least one of $R^1$, $R^2$, $R^3$, and $R^4$ is selected from the group consisting of higher aliphatic moiety, higher siloxyl moiety, higher aliphatic/siloxyl moiety, aliphatic/aryl moiety, siloxyl/aryl moiety, and aliphatic/siloxyl/aryl moiety; and
   the rest of $R^1$, $R^2$, $R^3$, and $R^4$ are selected from the group consisting of a $C_1$ to $C_4$ alkyl group, $(SiO)_1$ to $(SiO)_2$, and $C_n(SiO)_m$ where n is a number from 0 to 4 and m is a number from 0 to 2 and $n+m\leq 4$;
   where the higher aliphatic and/or siloxyl moiety is a hydrocarbon and/or siloxyl moiety having a straight chain length of linked atoms equivalent to that of a $C_5$ to $C_{25}$ straight chain, which may be substituted or unsubstituted, and may optionally contain one or more SiO unit, an ether or ester linkage or both.

4. The composition of claim 3, wherein the gas that liberates hydrogen ions in the presence of water is carbon dioxide and at least one of $R^1$, $R^2$, $R^3$, and $R^4$ is a higher aliphatic and/or siloxyl moiety.

5. The composition of claim 3, wherein at least one of $R^1$, $R^2$, $R^3$, and $R^4$ is an aliphatic and/or siloxyl moiety having a straight chain length of linked atoms equivalent to that of a $C_8$ to $C_{25}$ straight chain, which aliphatic and/or siloxyl moiety may be substituted or unsubstituted, and may optionally contain one or more SiO unit, an ether or ester linkage or both.

6. The composition of claim 5, wherein at least one of $R^1$, $R^2$, $R^3$, and $R^4$ is an aliphatic and/or siloxyl moiety having a straight chain length of linked atoms equivalent to that of a $C_{11}$ to $C_{25}$ straight chain, which aliphatic and/or siloxyl moiety may be substituted or unsubstituted, and may optionally contain one or more SiO unit, an ether or ester linkage or both.

7. The composition of claim 6, wherein the compound is N'-hexadecyl-N,N-dimethylacetamidinium bicarbonate or N'-dodecyl-N,N-dimethylacetamidium bicarbonate.

8. The composition of claim 2, wherein the gas that liberates hydrogen ions in the presence of water is carbon dioxide.

9. The composition of claim 1, wherein the gas that liberates hydrogen ions in the presence of water is carbon dioxide.

10. The composition of claim 1, wherein the nitrogen-containing portion comprises a protonated guanidine moiety.

11. The composition of claim 10, wherein the gas that liberates hydrogen ions in the presence of water is carbon dioxide.

12. The composition of claim 10, wherein the switchable surfactant compound comprises the general formula (5)

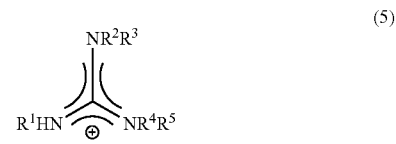

(5)

where
   at least one of $R^1$, $R^2$, $R^3$, $R^4$, and $R^5$ is selected from the group consisting of higher aliphatic moiety, higher siloxyl moiety, higher aliphatic/siloxyl moiety, aliphatic/aryl moiety, siloxyl/aryl moiety, and aliphatic/siloxyl/aryl moiety; and
   the rest of $R^1$, $R^2$, $R^3$, $R^4$, and $R^5$ are selected from the group consisting of a $C_1$ to $C_4$ alkyl group, $(SiO)_1$ to $(SiO)_2$, and $C_n(SiO)_m$ where n is a number from 0 to 4 and m is a number from 0 to 2 and $n+m\leq 4$;
   where the higher aliphatic and/or siloxyl moiety is a hydrocarbon and/or siloxyl moiety having a straight chain length of linked atoms equivalent to that of a $C_5$ to $C_{25}$ straight chain, which may be substituted or unsubstituted, and may optionally contain one or more SiO unit, an ether or ester linkage or both.

13. The composition of claim 12, wherein at least one of $R^1$, $R^2$, $R^3$, $R^4$, and $R^5$ is an aliphatic and/or siloxyl moiety having a straight chain length of linked atoms equivalent to that of a $C_8$ to $C_{25}$ straight chain, which aliphatic and/or siloxyl moiety may be substituted or unsubstituted, and may optionally contain one or more SiO unit, an ether or ester linkage or both.

14. The composition of claim 13, wherein at least one of $R^1$, $R^2$, $R^3$, $R^4$, and $R^5$ is an aliphatic and/or siloxyl moiety having a straight chain length of linked atoms equivalent to that of a $C_8$ to $C_{25}$ straight chain, which aliphatic and/or siloxyl moiety may be substituted or unsubstituted, and may optionally contain one or more SiO unit, an ether or ester linkage or both.

15. The composition of claim 1, wherein component (c) is a water immiscible liquid that is in a stable emulsion with said water or aqueous solution and forms an unstable emulsion or other two-phase mixture with said water or aqueous solution when the switchable surfactant compound is converted to the non-salt form.

16. The composition of claim 15, which additionally comprises a monomer for emulsion polymerization.

17. The composition of claim 1, wherein component (c) is a water insoluble solid that is in a stable suspension with said water or aqueous solution and forms an unstable suspension or other two-phase mixture with said water or aqueous solution when the switchable surfactant compound is converted to the non-salt form.

18. The composition of claim 1, wherein the flushing gas is nitrogen, argon, or air that has insufficient carbon dioxide to maintain said switchable surfactant compound in its salt form.

* * * * *

UNITED STATES PATENT AND TRADEMARK OFFICE
CERTIFICATE OF CORRECTION

PATENT NO. : 8,283,385 B2
APPLICATION NO. : 11/599623
DATED : October 9, 2012
INVENTOR(S) : Philip G. Jessop It is certified that error appears in the above-identified patent and that said Letters Patent is hereby corrected as shown below:

Column 34, Line 55, Claim 14

"$C_8$" should be --$C_{11}$--

Signed and Sealed this
Fourth Day of December, 2012

David J. Kappos
*Director of the United States Patent and Trademark Office*